United States Patent [19]

Crossley et al.

[11] Patent Number: 5,681,839
[45] Date of Patent: Oct. 28, 1997

[54] NITROGEN HETEROCYCLES

[75] Inventors: Roger Crossley, Reading; Albert Opalko, Maidenhead; Barry John Langham, Reading, all of England

[73] Assignee: John Wyeth & Brother, England

[21] Appl. No.: 448,453

[22] PCT Filed: Feb. 10, 1995

[86] PCT No.: PCT/GB95/00278

§ 371 Date: Dec. 7, 1995

§ 102(e) Date: Dec. 7, 1995

[87] PCT Pub. No.: WO95/21824

PCT Pub. Date: Aug. 17, 1995

[30] Foreign Application Priority Data

Feb. 10, 1994 [GB] United Kingdom ............. 9402561
Dec. 15, 1994 [GB] United Kingdom ............. 9425346

[51] Int. Cl.⁶ ..................... A61K 31/47; C07D 215/227
[52] U.S. Cl. ..................... 514/312; 546/157; 546/158
[58] Field of Search ..................... 546/157, 158; 514/312

[56] References Cited

U.S. PATENT DOCUMENTS

| | | | |
|---|---|---|---|
| 3,994,900 | 11/1976 | Krapcho | 514/312 |
| 4,576,949 | 3/1986 | Smith | 514/277 |
| 4,792,561 | 12/1988 | Walker | 514/312 |
| 4,921,862 | 5/1990 | Walker | 514/312 |
| 5,110,815 | 5/1992 | Effland | 514/228.2 |

FOREIGN PATENT DOCUMENTS

| | | |
|---|---|---|
| 55-27158 | 2/1980 | Japan. |
| 55-83750 | 6/1980 | Japan. |
| 1432378 | 4/1976 | United Kingdom. |
| 1463666 | 2/1977 | United Kingdom. |

OTHER PUBLICATIONS

Albrecht, Arch Pharm (Ewinheim), 318, pp. 1105–1115, 1985.
Zimmerman and Zeng, J. Org. Chem. 55(16), 4789–91 (1990).
Bennett and Minor, J. Het. Chem. 16(4), 633–35 (1990).
Albrecht and Shröder, Arch. Pharm (Weinheim) 308(8), 588–94 (1975).
Zymalkowski and Kothari, Arch. Pharm (Weinhiem) 303 (8), 667–75 (1970).
Reimann and Friesinger, Arch Pharm. (Weinheim), 318, 1105–1115 (1985).

Primary Examiner—C. Warren Ivy
Assistant Examiner—D. Margaret M. Mach
Attorney, Agent, or Firm—R. F. Boswell, Jr.

[57] ABSTRACT

This invention concerns a compound of generic formula

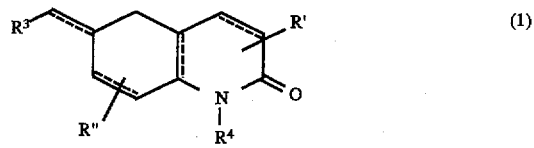

or a pharmaceutically acceptable salt thereof, where the dotted lines represent optional bonds, $R^3$ is an optionally substituted $C_6$–$C_{10}$ aryl or heteroaryl group;

$R^4$ represents hydrogen, or a group of formula —$CR^aR^bR^c$ where $R^a$, $R^b$ and $R^c$ are independently selected from hydrogen, $C_1$–$C_6$ alkyl $C_6$–$C_{10}$ aryl, heteroaryl, $C_1$–$C_6$ alkyl substituted by optionally substituted $C_6$–$C_{10}$ aryl or heteroaryl;

R' represents one or more optional substituents the same or different, selected from halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy($C_1$–$C_6$)alkyl, carboxy, $C_2$–$C_7$ alkanoxylamino, $C_6$–$C_{10}$ or heteroaryl or an ($C_6$–$C_{10}$ aryl)alkyl or a heteroaryl alkyl radical;

R" represents one or more optional mono- or di- valent substituents in the 5, 7 or 8 positions selected from $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, and R" can also represent hydroxy in the 6 position when the optional bond is absent; oxo and methylene;

which compounds have pharmaceutical uses conferred by their ability to block voltage gated potassium channels.

21 Claims, No Drawings

NITROGEN HETEROCYCLES

This application is a 371 of PCT/GB 95/00278, filed Feb. 10, 1995 published as WO95/21824 Aug. 17, 1995.

This invention relates to nitrogen heterocycles, more particularly to substituted quinolinones, partially or totally saturated, to processes for preparing them, and compositions containing them. The compounds have pharmaceutical uses conferred by their ability to block voltage gated potassium channels.

Voltage gated potassium ion ($K^+$) channels which produce transient outward currents (TOC) are present in the cell membranes of neurones and serve to repolarise the cell following a depolarisation by opening and allowing potassium ions to flow from the inside of the cell to the outside. They are, therefore, one of the main regulating influences on the nerve cell firing and determine the amount of current reaching the terminal regions of the cells. This in turn regulates the amount of neurotransmitter substances released from the nerve terminals. In addition, they help to determine the refractory period of the nerve cell and hence the probability of the cell firing again within a certain time. This governs neuronal excitability and also the tendency of a cell to undergo repetitive firing. An ability to modify the functioning of these channels by chemical means is likely to produce therapeutically useful agents. So far the agents which are known to block the TOC channels are toxins such as the snake toxin dendrotoxin, or 4-aminopyridine and its derivatives. Blockade of the TOC channels leads to a change in the pattern of transmitter release and depending upon the pattern and type of neurone affected different therapeutic ends will result. For example TOC blockers which increase dopaminergic transmission in the substantia nigra will be of use in treatment of Parkinson's disease. Likewise, an increase in cholinergic function is of use in Alzheimer's disease and in cognition enhancement. Because of the complicated neural networks in the brain blockade of the TOC may also lead to increase in more than one transmitter substance at a time and this can act synergistically where a disease state is associated with more than one transmitter deficit as is often the case. It is evident, therefore that TOC blockers may be of use in areas of depression, pain, psychoses, cognition, memory and learning, anxiety, Parkinson's disease and Alzheimer's disease. In addition they can be used as a treatment for conditions where there is an impairment of nerve transmission such as multiple sclerosis.

Compounds which act to increase channel function may be termed channel openers and these serve to increase the braking action of the channels on the cells. In this respect they will also reduce the likelihood of the cells to undergo repetitive firing and may be used as anticonvulsants in the treatment of epilepsy. Also, their action to reduce neurotransmitter release means that they may be used as anaesthetics, analgesics, sedatives and anxiolytics.

This invention provides compounds of generic formula (I):

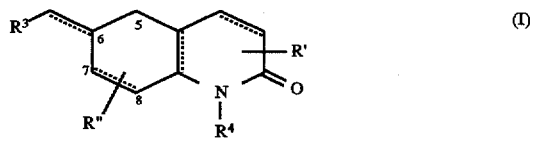

or a pharmaceutically acceptable salt thereof, where the dotted lines represent optional bonds, $R^3$ is an optionally substituted $C_6$–$C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl; $C_1$–$C_6$ alkoxy or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy) carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$) aroyloxy; ($C_1$–$C_6$)alkylcarbonylamino, ($C_6$–$C_{10}$aryl) carbonylamino; ($C_2$–$C_7$) alkoxycarbonylamino; $C_6$–$C_{10}$ aryl; heteroaryl as defined above; or $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^3$;

R' represents one or more optional substituents the same or different, selected from one or more of the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxylamino, optionally substituted $C_6$–$C_{10}$ or heteroaryl or an optionally substituted ($C_6$–$C_{10}$ aryl)alkyl or a heteroaryl alkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy ($C_1$–$C_6$)alkyl; ($C_1$–$C_6$alkoxy)carbonyl; amino including substituted amino, e.g mono- or di- ($C_1$–$C_6$ alkyl) -amino; nitro; hydroxy; mercapto; $C_1$–$C_6$alkylthio; ($C_1$–$C_6$alkyl)carbonyl; ($C_6$–$C_{10}$ aryl)carbonyl; ($C_2$–$C_7$) alkanoyloxy; ($C_7$–$C_{11}$)aroyloxy; ($C_1$–$C_6$alkyl) carbonylamino, ($C_6$–$C_{10}$aryl)carbonylamino; ($C_2$–$C_7$ alkoxycarbonyl)amino; $C_6$–$C_{10}$ aryl; heteroaryl as defined above; or $C_1$–$C_2$ alkylenedioxy; and R" represents one or more optional mono- or di- valent substituents in the 5, 7 or 8 positions the same or different: monovalent substituents being selected from the following:$C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, R" can also represent hydroxy in the 6 position (when the optional bond is absent); the di-valent substituent being oxo (i.e =O).

In a subgeneric aspect this invention provides compounds of formula IA:

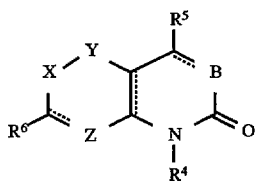

(IA)

or a pharmaceutically acceptable salt thereof,
wherein the dotted lines represent optional bonds with the nitrogen ring optional bonds being between any adjacent ring atoms subject to valency considerations, B is a group of formula

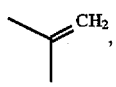

(iii)

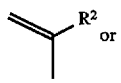

(iv)

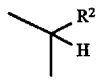

(v)

wherein
$R^2$ is hydrogen, $C_1$–$C_6$ alkyl, $C_1$–$C_6$ hydroxyalkyl, $C_2$–$C_7$ alkanoyloxy($C_1$–$C_6$)alkyl, $C_2$–$C_7$ alkoxycarbonyl, cyano, aminocarbonyl, carboxy or $C_2$–$C_7$ alkanoylamino;

X is a group of formula

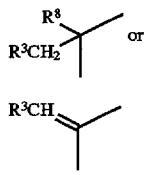

(vii)

(viii)

where
$R^8$ is H or OH;
$R^3$ is a $C_6$–$C_{10}$ aryl or a heteroaryl radical containing 5 to 10 ring atoms of which one or more (e.g up to 3) of said atoms are heteroatoms selected from oxygen, nitrogen and sulphur, the same or different; said aryl or heteroaryl radical being optionally substituted by one or more substituents the same or different selected from halogen or a $C_1$–$C_6$ alkyl, optionally substituted $C_6$–$C_{10}$ or heteroaryl or an optionally substituted ($C_6$–$C_{10}$ aryl)alkyl or a heteroarylalkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g mono- or di-($C_1$–$C_6$ alkyl)-amino; nitro; hydroxy; mercapto; $C_1$–$C_6$alkylthio; ($C_1$–$C_6$ alkyl) carbonyl; ($C_6$–$C_{10}$ aryl) carbonyl; ($C_2$–$C_7$)alkanoyloxy; ($C_7$–$C_{11}$)aroyloxy; ($C_1$–$C_6$ alkyl)carbonylamino, ($C_6$–$C_{10}$aryl) carbonylamino; ($C_2$–$C_7$) alkoxycarbonylamino; $C_6$–$C_{10}$ aryl; heteroaryl as defined above; or $C_1$–$C_2$ alkylenedioxy;

Y is

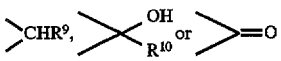

where $R^9$ represents hydrogen, $C_1$–$C_6$ alkyl, $C_2$–$C_7$ alkanoyloxy, optionally substituted heteroaryl, optionally substituted $C_6$–$C_{10}$ aryl or $CH_2OH$; and $R^{10}$ represents hydrogen or $C_1$–$C_6$ alkyl;

and $R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^2$;

Z is C=O, —$CHR^7$— or =C($R^7$)— where $R^7$ is hydrogen, OH, $CH_2OH$, $NH_2$, $C_2$–$C_7$ alkanoyloxy, $C_2$–$C_7$ alkanoylamino $C_1$–$C_6$alkylamino or a $C_1$–$C_6$ alkyl group optionally substituted by a group $R^3$ as defined above;

$R^5$ is hydrogen, $C_1$–$C_6$ alkyl, $C_6$–$C_{10}$ aryl, heteroaryl or a $C_1$–$C_6$alkyl substituted by $C_6$–$C_{10}$ aryl or heteroaryl; said aryl or heteroaryl groups being optionally substituted as defined for $R^2$ above;

$R^6$ is $NH_2$, $C_7$–$C_{17}$ aralkanoylamino, $C_2$–$C_7$ alkanoylamino or $R^6$ is one of the values listed for $R^5$ above.

Included in the projected formula covered by formula I (and IA) above are the following (where Z is $CH_2$, and $R^5$ and $R^6$ are hydrogen):

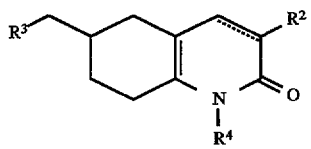

i.e  B = formula (iv) or (v)
     X = formula (vii)
     Y = $CH_2$
(Examples 1, 3, 5, 9,16, 17)

i.e  B = formula (v)
     X = formula (vii)
     Y = $CH_2$
(Examples 2, 4, 6, 7, 8, 10, 11, 12, 13, 14, 15, 20, 21, 22, 23, 24, and 26–31

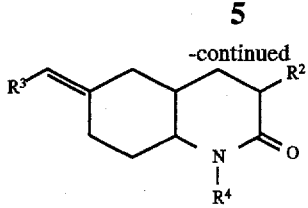

ie  B = formula (v),
    X = formula (vii),
    Y = CH₂,
Example 25; E and Z isomers)

in which formulae above the dotted line represents an optional bond.

In all the formulae above, examples of alkyl as a group or pan of a group, e.g aralkyl, alkanoyl, are straight or branched chain groups of up to 6 carbon atoms especially of 1 to 4 carbon atoms such as methyl, ethyl, n-propyl, isopropyl, n-butyl and sec butyl. Examples of "alkoxy" as a group or pan of a group, e.g alkoxycarbonyl, are groups of formula alkyl-O— where alkyl has the meanings immediately above.

In the formulae above examples of aryl as a group or part of a group, e.g aralkyl, aralkanol, are mono- or bicyclic groups of 6 to 10 carbon atoms such as phenyl and naphthyl, e.g 1 or 2-naphthyl. Heteroaryl groups have heteroatoms selected from oxygen, nitrogen and/or sulphur. Examples of heteroaryl as a group or pan of a group, e.g heteroarylalkyl, are mono- or bicyclic groups of 5 to 10 ring atoms such as those having one nitrogen heteroatom e.g 2 or 3-pyrrolyl, 2, 3 or 4-pyridyl, quinolyl (e.g 2, 3 or 6-quinolyl) isoquinolyl (e.g 1-, 3- or 6-isoquinolyl); one sulphur atom, e.g 2- or 3-thienyl or benzothienyl (e.g 2, 3 or 6-benzothienyl); or one oxygen atom, e.g 2- or 3-furanyl or benzofuranyl (e.g 2-, 3- or 6-benzofuranyl); or two or more heteroatoms, e.g thiazolyl (e.g 2-thiazolyl), imidazolyl (e.g 2-imidazolyl); oxazolyl (e.g 2-oxazolyl).

Examples of optional substitutents are alkyl, alkoxy, aryl and heteroaryl as illustrated above, chlorine, bromine, fluorine, CF₃, CH₂F, CF₃CH₂, HOCH₂—, HOCH(Me)—, HO(CH₂)₂—, MeOOC—, EtOOC—, NH₂, NHMe—, NHEt—, NMe₂—, NO₂, HO, HS—, MeS—, EtS—, CH₃CO—, EtCO—, PhCO—, CH₃CONH—, EtCONH—, PhCONH—, MeOOCNH—, EtOOCNH—, CH₃CO.O—, EtCO.O— or methylene- or ethylene-dioxy.

The group B may be for example =CH—, =C(CH₃)—

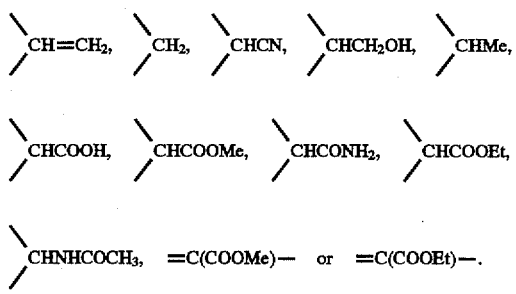

R³ may be for example phenyl or phenyl substituted by one or more substitutents as illustrated above, e.g substituents the same or different selected from: $C_1$–$C_6$ alkoxy such as methoxy, ethoxy; halogen such as chlorine or bromine; CF₃; CF₃O; $C_1$–$C_6$ alkyl such as methyl or ethyl; hydroxy; cyano and carboxy. Preferred values for R₃ are methoxyphenyl, e.g 4-methoxyphenyl and hydroxyphenyl, e.g 4-hydroxyphenyl.

Examples of the group Y are CH₂, CO, C=CH₂, CHOH or CHOCOCH₃, (i.e in formula I, R" is absent, =O, =CH₂, OH or OCOCH₃ respectively).

The value of R⁴ is for example hydrogen or a group of formula —CR$^a$R$^b$R$^c$ where R$_a$ and R$_b$ are independently selected from hydrogen, methyl, ethyl, propyl, isopropyl or butyl and R$^c$ is selected from hydrogen, methyl, ethyl, isopropyl, propyl, butyl or a $C_6$–$C_{10}$ aryl or a heteroaryl group containing 5–10 ring atoms of which one or more of said atoms are heteroatoms selected from oxygen, nitrogen and sulphur in which said aryl and heteroaryl moieties are optionally substituted as illustrated above.

Preferably R$_a$ is hydrogen, R$_b$ is methyl and R$^c$ is optionally substituted aryl such as phenyl or substituted phenyl such as illustrated above.

The group Z may be for example C=O, —CH₂—, —CH(Me); —CH(Ph)—, =CH(Me)— or —CH(CH₂Ph)—, (i.e in formula I, R" represents =O, absent, Me, Ph, Me or CH₂Ph).

Examples of R⁵ are hydrogen, $C_1$–$C_4$ alkyl, e.g methyl, phenyl, benzyl and substituted phenyl where substituents are as defined hereinabove.

Examples of R⁶ are hydrogen, NH₂ and NHCOCH₃.

Preferred compounds of formula I and IA have R³ represents 4-methoxy-phenyl. Also preferred are compounds where R² represents methyl or hydrogen.

Particularly preferred are compounds of formula (IB):

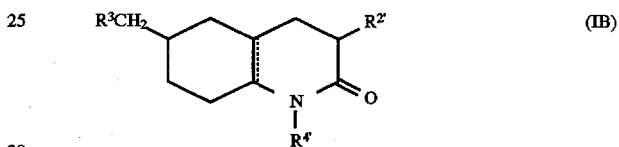

in which formula R²' is hydrogen, $C_1$–$C_6$ alkyl, $C_2$–$C_7$ alkoxycarbonyl, acetylamino, CN or CH₂OH; R³ is as defined above, preferably unsubstituted or substituted phenyl, e.g where the substituents is/are selected from $C_1$–$C_6$ alkyl, $C_1$–$C_6$ alkoxy, hydroxy, halogen and methylene or ethylene-dioxy; and R⁴' is hydrogen, alkyl or optionally substituted aryl($C_1$–$C_6$) alkyl in which the alkyl group is itself optionally substituted by $C_1$–$C_6$ alkyl.

Examples of R⁴' include phenylmethyl or α-methylphenylmethyl in which the phenyl group is optionally substituted by substituents as listed above.

Preferred values for R⁴' are PhCH(Me)—, PhCH₂— and H.

The compounds of formula I (including subgeneric formulae IA and IB) possess one or more (e.g four, five or six) asymmetric centres and accordingly the compounds may exist and be isolated in a number of optically active stereoisomeric forms. When X has formula viii then geometric isomers (E,Z) are also obtained. This invention encompasses the compounds of formula I in any optically active or geometric form or mixtures thereof eg, racemates or diastereoisomers. Standard separation techniques may be used to isolate particular enantiomeric and diastereomeric forms. For example a racemic mixture may be converted to a mixture of optically active diastereoisomers by reaction with a single enantiomer of a 'resolving agent' (for example by diastereomeric salt formation or formation of a covalent bond). The resulting mixture of optically active diastereoisomers may be separated by standard techniques (e.g crystallisation or chromatography) and individual optically active diastereoisomers then treated to remove the 'resolving agent' thereby releasing the single enantiomer of the compound of the invention. Chiral chromatography (using a chiral support, eluent or ion pairing agent) may also be used to separate enantiomeric mixtures directly. Stereospecific synthesis using optically active starting materials and/or chiral reagent catalyst and/or solvents may also be employed to prepare particular diastereoisomers or even a particular enantiomer. For example where the compound of formula I is prepared by an addition process creating one or more optical centres then carrying out the reaction using a chiral catalyst or agent or in a chiral environment can give the product as a single enantiomer.

Compounds of formula I can have one asymmetric centre at the 6-position. and such compounds can be isolated as the R- or S-enantiomers or as the racemates. In the saturated or partially saturated systems, e.g hexahydro-quinolinones or octahydroquinolinones where the bridgehead carbons 4a and 8a are linked by a single bond, then two further chiral centres (4a and 8a) are present and the compounds can be isolated as the individual enantiomers. In addition position 3 may also be a chiral centre. When $R^4$ represents an aryl alkyl (alkyl)- or heteroaryl-alkyl(alkyl)-moiety then yet a further chiral centre is present. All such enantiomers and diasteresoisomers of the compounds of formula I are included in this invention.

The compounds of formula I possess pharmacological activity in particular they block voltage gated potassium channels. They may therefore be used to treat CNS disorders as described above such as depression, pain psychoses, anxiety, movement disorders (such as Parkinson's disease) and multiple sclerosis and in enhancing cognition, memory and learning. They demonstrate their ability to block voltage gated potassium channels in dorsal root ganglion cells by the following standard test procedures:

Procedure 1

Modulation of voltage-activated $K^+$ currents in dorsal root ganglion (DRG) cells:

The method used in the culture or dorsal root ganglion cells is similar to that described by Wood et. al., Capsaicin induced ion fluxes in dorsal root ganglion cells in culture, J. Neuroscience, 8, 3208–3220) (1988). Dorsal root ganglia are dissected mainly from around the lumbar and thoracic vertebrae and placed in a conical centrifuge tube containing Ham's F14 nutrient mixture (F14:Imperial Laboratories) plus horse serum (HS: GIBCO or Flow). When all ganglia have been collected (ex ca. 14 pups) the excess medium is removed and the ganglia incubated for 30 min in "F14+HS" containing 0.1% collagenase Type 1A-S (Sigma). Excess medium is removed, ganglia washed in 4 ml F14 (no HS), resuspended and spun down at 900 g for 10s. The supernatant is again removed and replaced with 1.8 ml F14 (no HS) plus 0.2 ml trypsin (GIBCO) at a final concentration of 0.25%. The ganglia are then incubated at 37° C. for 30 min agitating every 10 min to prevent clumping. The trypsinisation is inhibited by the addition of 6 ml "F14+HS" and cells are resuspended and centrifuged as before. The medium is removed and 2 ml added of "F14+HS" containing 0.4% DNAase 1 (Sigma). The ganglia are then triturated gently 15–20× using a siliconised pasteur pipette, filtered through a 90 mm nylon mesh filter and collected into a centrifuge tube. The filter is further washed with 2 ml of "F14+HS" which is collected into the same tube. The suspension is spun at 900 g for 3 min, the supernatant removed and the cells resuspended in DRG Growth Medium (DRG-GM) which consists of: HAMS F14 nutrient mixture (40%, v/v), HS(10%, v/v) C6 conditioned medium (50%, v/v), penicillin/streptomycin (100 U/ml; 100 µg/ml) and NGF (30 µg/ml). Cells are then plated out onto five 60 mm poly-L-lysine-coated tissue culture petri dishes (see below).

Replating

After a few days in culture (3–7 days, usually), cells are resuspended from 60 mm dishes using a 0.25% solution of trypsin in F14. An equal volume of DRG-GM is added to inhibit the trypsin, the cells are spun at 900 g for 5 minutes and resuspended in 0.25–0.5 ml of DRG-GM. Neurites are removed by gentle trituration through a 21 g syringe needle (15–20 strokes) and a drop of the cell suspension is then placed on each of 5–6 poly-D-lysine- and laminin-coated 35 mm petri dishes (see below). After 30 minutes incubation at 37° C., each plate is flooded with ca 1.5 ml DRG-GM and after about 1 hour incubation, cells are ready for electrophysiological recording. This final step is carried out specifically in order to remove neurites which hinder good voltage-clamp of the cells.

Coating of plates:

2 ml of poly-D-lysine (Sigma), reconstituted in distilled water to 100 µg/ml, are added to each plate and left for 1–2 hours. Plates are then washed with water and left to dry. Laminin (5 µg/ml) is added as a drop to the centre of plates (previously coated with poly-D-Lys), left for 45 min before removal of excess and use of plates.

Electrophysiology:

Recordings are made using an AxoClamp-2A (Axon Instruments Inc) switiching clamp amplifier using patch electrodes (4–8 Mohms), made from borosilicate glass capillary tubes (GC150TF-10, Clark Electromedical) and fire-polished. Electrodes are filled with (in mM): 140K Gluconate, 2 $MgCl_2$, 1.1 EGTA/KOH, 5 HEPES, 20 sucrose, 2 MgATP, 0.2 GTP; pH set to 7.2 with KOH and osmolarity adjusted with sucrose to 310 mOsm. The electrodes are then and dipped in Sigmacote (Sigma) prior to recording to reduce stray capacitance. The bathing solution in which cells are continually perfused (during recordings) consists of (in mM): 124 NaCl, 2.5 KCl, 4 $MgCl_2$, 5 HEPES, 10 glucose, 1 µM TTX, 20 sucrose pH set to 7.4 with NaOH and osmolarity adjusted with sucrose to 320 mOsm. $Ca^{2+}$ is omitted from the bathing medium in order to minimise voltage-activated $Ca^{2+}$ currents and $Ca^{2+}$ activated $K^+$ currents. TTX is included to block voltage-activated $Na^+$ currents, although in some recordings a residual TTX-resistant $Na^+$ current is evident. Recordings are made in voltage-clamp mode using a voltage-step protocol consisting of:

i) holding potential $(V_h)=-30$ mV (to inactivate transient outward current)
ii) 1s prepulse to −100 mV
iii) 1s pulse to +60 mV to activate total outward current
iv) return to −30 mV In some cases current-voltage(I-V) relationships are obtained in the presence and absence of test compound by constructing families of voltage steps over a range of membrane potentials (−100 mV to +60 mV) from a holding potential of either −30 mV or −100 mV. Voltage steps and data acquisition (current responses) are controlled by an Atari MegaSTE computer interfaced to the voltage-clamp via an ITC-16 ADC/DAC (Instrutech Corp.) and subsequent analysis carried out using REVIEW (Instrutech Corp). Test compounds are applied to individual neurones by a local microperfusion system, initially at a test concentration of 100 or 10 µM(solubility-permitting).

Calculations:

Current responses during the test voltage step to +60 mV (above) are measured off-line using REVIEW (Instrutech Corp). The following measurements are made: peak (with ca.50 ms) and Q integral (t=1s) outward current measured at +60 mV:

i) after conditioning prepulse to −100 mV (includes non-inactivating as well as transient outward current (TOC)

ii) without conditioning prepulse (mainly non-inactivating current)

iii) difference (digital subtraction) of above currents corresponds to TOC). Current amplitudes are obtained for: total outward current ($K_{-100}$), noninactivating current ($K_{-30}$) and TOC. Peak current amplitudes recorded in the presence of test compounds are expressed as a percentage of the corresponding control values.

Standard Compounds:

4-aminopyridine (100% block of TOC at 1 mM)

Toxin I (50% block of TOC at 100 nM) (Toxin I is a dendrotoxin homologue.)

The compounds were also tested for blocking transient outward potassium currents (TOC) in the $GH_3$ rat pituitary cell line according to the procedure below:

Procedure 2

$GH_3$ cells were obtained from either Flow Laboratories or European Centre for Animal Cell Cultures (Potion Down), and maintained in tissue culture using standard procedures and media for this cell line. Cells were plated on 35 mm plastic dishes and used subsequently for electophysiology within 1 to 10 days. Currents were recorded using the whole-cell voltage clamp configuration of the patch-clamp technique, using an Axopatch 1C amplifier (Axon Instruments). Patch electrodes were manufactured from aluminosilicate glass tubing (Clark Electomedical SM150F-10) and heat polished prior to use. Resistance was 1–5 MΩ. No electrode coating was necessary for whole-cell recording. Signal acquisition and analysis was performed using pClamp software (Axon Instruments). A p-on-4 subtraction procedure was used to remove leak and capacitative currents on line. A holding potential of −100 mV was routinely used: this avoided accumulation of slow voltage-dependent inactivation. Two main protocols were used in testing drugs. 1) Current-voltage (I-V) curves were collected, with incrementing steps of either 10 or 20 mV. Full I-V curves were obtained both in control and drag solutions. 2) a 'pharmacology' program, which involved single voltage steps fromm −100 to +60 mV, applied and collected at 20s intervals. Compounds under investigation were applied via a 'U' tube rapid application system to a small area of the recording chamber. Drug applications were always bracketed by control solutions to ensure reversibility. The recording chamber was continuously perfused at 1–5 ml.min$^{-1}$. Results are expressed as % of control peak current (step from −100 to +60 mV). However, where drugs have a time dependent effect on TOC, i.e acceleration of TOC decay, results are also expressed as a % of total charge transferred within a defined period of the voltage step from −100 to +60 mV. The standard extracellular solution contained (in mM): NaCl 135 (or choline or TRIS chloride); KCl 5; $MgCl_2$ 4; EGTA 1; TEACl 10; HEPES 10; glucose 25; pH set to 7.4 with NaOH. TTX was usually included at 100–200 nM. The intracellular (pipette) solution was comprised of (in mM): K aspartate 120; KCl 20; $MgCl_2$ 1; cAMP 1; MgATP 2; EGTA 10; HEPES 10; pH 7.4 with KOH. Other intracellular substrates were often used without noticeable effect. This solution was stored in 1 ml aliquots at −4° C., and filtered at 0.2 μm. These recording solutions precluded activation of voltage dependent Na, Ca, delayed rectifier and Ca-activated K currents. The resulting whole-cell currents chiefly comprised the transient outward potassium current, switching on with third power kinetics reaching peak amplitudes of ~1 nA at +60 mV, and a double exponential decay (time constants of ~30 and 160 ms at +60 mV). There is no significant change in current amplitude within the normal recording period, which may extend for up to 90 min. One dish of cells usually lasts several hours.

The standard compound 4-aminopyridine is a block @ 1–5 mM. (80% block at 5 mM).

RESULTS

Results for representative compounds of this invention in the two abovementioned tests are shown in the Table below:

| | | % Block of TOC | |
|---|---|---|---|
| COMPOUND EXAMPLE NO | CONCEN-TRATION | PROCEDURE 1 DRG % | PROCEDURE 2 GH3 % |
| 8 | 200 μM | — | 54 |
| 13 | 100 μM | 24 | 45 |
| 17 | 100 μM | — | 35 |
| 22 | 100 μM | — | 34 |
| 30 | 10 μM | 33 | — |

This invention also provides processes for preparing the compounds of formula I and IA. Many starting materials used herein can be derived from substituted catechols, reduced to give or form many known cyclohexane-1,3- or -1,4-diones appropriately protected to give compounds of the type:

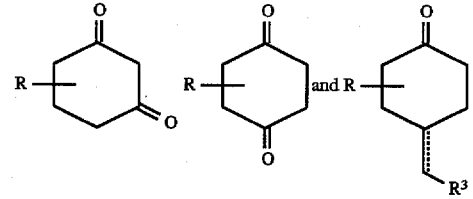

where R is R" or a group convertible thereto, and $R^3$ is is as defined herein. Such compounds can be converted to final products or other starting materials as described herein via known pyridine ring syntheses for example: Comprehensive Organic Chemistry, Vol. 4, Editor P G Samroes, Part 16.1, pages 3–84, Pyridines, by D M Smith, Pergamon Press; Comprehensive Heterocyclic Chemistry Vol. 2, Editors Boulton and McKillop Part 2A, "Six membered rings with one nitrogen atom", Pergamon Press and The Chemistry of Heterocyclic Compounds. Editor A Weissberger, Pyridine and Its Derivatives, Parts 1–4, (1962), Interscience Publishers.

Once a pyridine ring system is obtained it can be reduced, completely or partially as described in the literature to give saturated or partially saturated ting systems which themselves may be final products or starting materials.

Compounds of formula I are therefore useful for preparing other compounds of formula I as will be apparent from the processes described herein. Compounds of formula I may be prepared by one of the following processes where if necessary reactive substituent groups are protected prior to reaction and removed thereafter; said processes comprising:

(A) reacting a compound of formula:

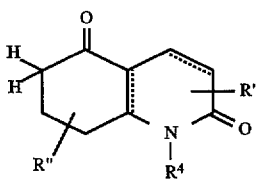

(II)

wherein the dotted lines, R', R" and $R^4$ are as defined herein with an aldehyde of formula $R^3$CHO, in the presence of base to give a corresponding compound of formula I which has oxo group in the 5-position and the optional bond to the 6-position is present, or (B) reacting a compound of formula:

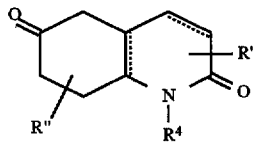

(III)

wherein R', R" and $R^4$ are as defined above with an artion of formula:

$R^3CH_2^\ominus$ where $R^3$ is as defined above, e.g using a Grignard reagent, to give a corresponding compound of formula I having a 6-hydroxy group, which compound may be dehydrated to give a compound of formula I wherein the optional bond to the 6-position is present; or (C) reacting a compound of formula (III) as defined above with a Wittig reagent of formula:

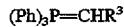

$(Ph)_3P=CHR^3$ wherein $R^3$ is as defined above to give a corresponding compound of formula I where the optional bond to the 6-position is present; or (D) reacting a compound of formula (IV):

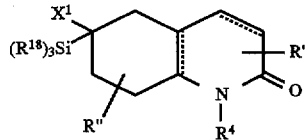

(IV)

wherein R', R", and $R^4$ are as defined above, $(R^{18})_3$ is defined as three $R^{18}$ radicals the same or different selected from alkyl, cycloalkyl, aralkyl, aryl or electron donating substituents such as alkoxy, cycloalkoxy, aralkoxy, aryloxy, alkylthio, cycloalkythio, aralkylthio or arylthio, the group $R^dR^eN$- where $R^d$ and $R^e$ are selected from alkyl, cycloalkyl, aryl and aralkyl or $R^d$ and $R^e$ are joined to form a heterocyclic ring with the nitrogen atom to which they are attached (e.g piperidinyl, pyrrolidinyl which may be substituted, e.g by alkyl) and $X^1$ is sodium, potassium or lithium, with a compound of formula:

$R^3CHO$ wherein $R^3$ is as defined above in connection with formula I; followed by treatment under acidic or basic conditions, to give a compound of formula I in which the optional bond to the 6-position is present; or (E) reacting a compound of formula (III) as defined above with a compound of formula:

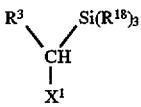

(V)

where $R^3$, $R^{18}$ and $X^1$ are as defined above, followed by treatment under acidic or basic conditions, or (F) convening a compound of formula I having at least one reactive substituent group or site to give a different compound of formula I; or (G) reducing a compound of formula (L):

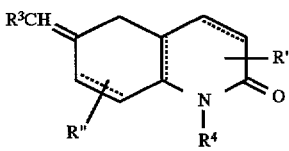

(L)

wherein R', R", $R^3$ and $R^4$ are as defined above e.g catalytically using 5% Pd/C and hydrogen; to give a compound of formula I wherein the optional bond to the 6-position is absent; or (H) alehydrating a compound of formula (M):

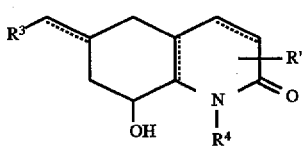

(M)

wherein the dotted lines, R', $R^3$ and $R^4$ are as defined above, e.g. using polyphosphoric acid and warming, to give a compound of formula I having a double bond between the 7 and 8 positions, or (I) converting a basic compound of formula I to an acid addition or quaternary ammonium salt thereof, or vice versa, or (J) resolving a mixture of isomeric compounds of formula I to isolate a specific enantiomeric form substantially in the absence of other isomers.

Processes for preparing the subgeneric aspects of this invention, e.g compounds of formula IA comprise one of the following:

a) cyclising a compound of formula:

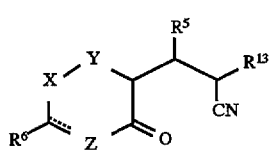

(VI)

wherein $R^5$, $R^6$, X, Y and Z are as hereinbefore defined and $R^{13}$ is hydrogen, hydroxy($C_1$-$C_6$)alkyl, ($C_2$-$C_7$alkanoyl)oxy($C_1$-$C_6$)alkyl, ($C_1$-$C_6$ alkoxy) carbonyl or $C_1$-$C_6$ alkyl to give a corresponding compound of formula IA having a bridgehead double bond wherein $R^4$ is hydrogen and B is

where $R^2$ is hydrogen, $C_2$-$C_7$alkoxycarbonyl, hydroxy($C_1$-$C_6$)alkyl, ($C_2$-$C_7$alkanoyl)oxy($C_1$-$C_6$)alkyl or $C_1$-$C_6$ alkyl; or b) reacting a compound of formula:

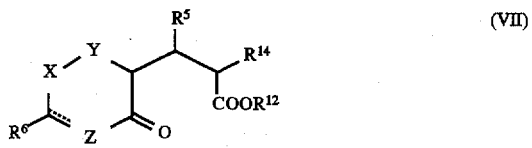 (VII)

where $R^{14}$ is H, CN, ($C_1$–$C_6$alkoxy)carbonyl, hydroxy ($C_1$–$C_6$)alkyl, ($C_2$–$C_7$alkanoyl)oxy($C_1$–$C_6$)alkyl, or $C_1$–$C_6$ alkyl; and $COOR^{12}$ is an ester group (e.g $R^{12}$ is an organic radical such as alkyl or aralkyl) and $R^5$, $R^6$, X, Y and Z are as defined above, with a compound of formula $R^4NH_2$ where $R^4$ is as defined above, (e.g an amine or an ammonia source such as ammonium acetate) and cyclising to give a corresponding compound of formula IA having a bridgehead double bond wherein $R^4$ are as defined above and B is

where $R^2$ is hydrogen, ($C_1$–$C_6$alkoxy)carbonyl, hydroxy($C_1$–$C_6$)alkyl, ($C_2$–$C_7$alkanoyl)oxy($C_1$–$C_6$) alkyl, CN or $C_1$–$C_6$ alkyl; or c) cyclising a compound of formula (VIII):

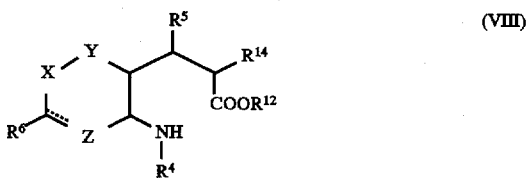 (VIII)

wherein X, Y, Z, $R^4$, $R^5$, $R^6$, $R^{14}$ and $COOR^{12}$ are as defined above to give a corresponding compound of formula IA (where the nitrogen ring dotted lines are all absent) wherein B is

where $R^2$ is hydrogen, ($C_1$–$C_6$ alkoxy)carbonyl, hydroxy($C_1$–$C_6$)alkyl, ($C_2$–$C_7$alkanoyl)oxy($C_1$–$C_6$) alkyl, CN or $C_1$–$C_6$ alkyl: or d) reacting a compound of formula (IX):

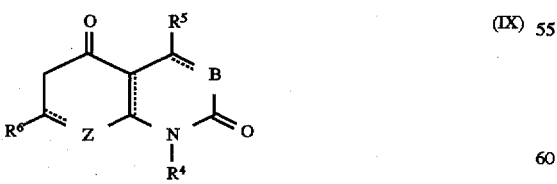 (IX)

wherein the dotted lines B, Z, $R^5$, $R^6$ and $R^4$ are as defined above, with an aldehyde of formula $R^3$ CHO, in the presence of base to give a corresponding compound of formula IA wherein X is formula (viii) and Y is C=O; or e) reacting a compound of formula (X):

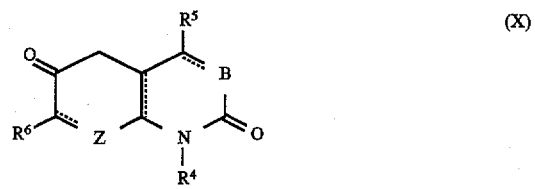 (X)

wherein B, Z, $R^5$, $R^6$ and $R^4$ are as defined above, with an ylide of formula:

$(Ph)_3P=CHR^3$ (XI)

wherein $R^3$ is as defined above to give a corresponding compound of formula IA wherein X has formula (viii):

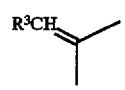 (viii)

or (f) reacting a compound of formula:

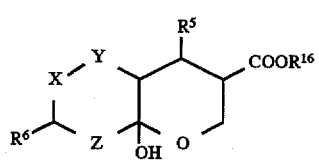 (XII)

wherein X, Y, Z, $R^5$, $R^6$ are as defined above and $R^{16}$ is $C_1$–$C_6$ alkyl with a compound of formula $R^4NH_2$ as defined in process step b) to give a corresponding compound of formula IA having a double bond between bridgehead carbons, and B has formula (v) where $R^2$ is $CH_2OH$ and $R^4$ is as defined above, or g) reducing a compound of formula IA having a double bond between the bridgehead carbons of structure (N):

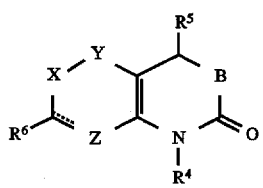 (N)

wherein B, X, Y, Z, $R^4$, $R^5$ and $R^6$ are as defined above to give a corresponding nitrogen ring saturated compound of formula IA, having a single bond between bridgehead carbons, of structure (O):

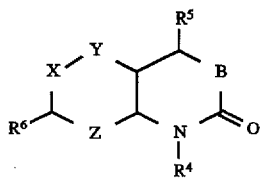 (O)

or h) convening any substituent group present in a compound of formula IA to another substituent group by known means; e.g reducing $R^2$ is ($C_1$–$C_6$alkoxy)-carbonyl to give a compound of formula IA wherein $R^2$ is —$CH_2OH$ or i) reducing a compound of formula IA wherein Y is

i.e a compound of formula:

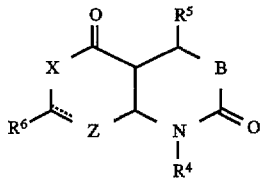
(IR)

wherein the dotted lines, B, X, Z, $R^4$, $R^5$ and $R^6$ are as defined above, to give a corresponding compound of formula I wherein Y is $CH_2$; or j) reducing a compound of formula IA wherein X has formula (viii) to give a compound of formula IA wherein X has formula (vii) and $R^8$ is hydrogen; or k) hydrogenating a compound of formula IA where $R^4$ is a group of formula $CR^aR^bR^c$ wherein at least one of $R^a$, $R^b$ and $R^c$ is optionally substituted aryl to give a compound of formula IA wherein $R^4$ is hydrogen; or l) reacting an anionic compound of formula (S):

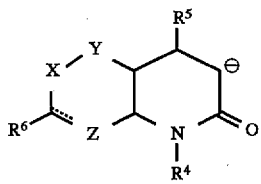
(S)

wherein the dotted line, X, Y, Z, $R^4$, $R^5$ and $R^6$ are as defined above, with an electrophile containing the $R^2$ moiety for example $R^2L$ where L is a leaving group to give a corresponding compound of formula IA wherein B has formula (v) wherein $R^2$ is hereinbefore defined; or m) resolving a mixture of isomeric compounds of formula IA using standard separation techniques to isolate a specific enantiomeric form in the absence of other isomers, or n) alkylating or aralkylating a compound of formula IA wherein $R^4$ is hydrogen to give a compound of formula IA wherein $R^4$ is $R^a$, $R^b$ or $R^c$.

Methods for carrying out processes (A)–(J) and (a)–(n) are known in the literature and may be carried out by standard procedures. If required other sites in the molecule can be protected by known methods to avoid side reactions.

With regard to process (a) the cyclisation can be conveniently carried out at room temperature or below using concentrated HBr in acetic acid to give a hexahydroquinolin-2[1H]-one.

Processes b) and f) may be carried out with heating if required using an inert solvent, e.g methanol when an ammonium source such as ammonium acetate is used to form the lactam, or toluene when primary amines are used. The reaction with primary amines is preferably carried out the presence of a weak acid e.g glacial acetic acid under reflux.

Process c) is conveniently carried out under neutral or basic conditions, e.g basifying with sodium carbonate without heating when $R^4$ is hydrogen. When $R^4$ is other than hydrogen the reaction may be carried out using toluene solvent preferably in the presence of a weak acid, e.g glacial acetic acid under reflux if necessary.

Processes d) and A) are conveniently carried out by heating in the presence of a small amount of organic base, e.g piperidine.

Process B) may be carried out by reacting with a Grignard reagent of formula $R^3CH_2Mghal$ where hal is a halogen such as bromine.

Processes e) and C) may be carried out under Wittig reaction conditions using the desired substituted triphenylphosphonium halide. Processes for carrying out Wittig reactions are extensively described in the literature. See for example Org. React. 14, 270 (1965) and Org. Syn. Coll. Vol. 5 751 (1973).

Process (D) may be carried out under Peterson reaction conditions. In the process an intermediate of formula IV in which $X^1$ is $R^3CH(OX)$— (X is Li, Na or K) is formed and this compound is hydrolysed to the alcohol and dehydrated by acid or base treatment, removing any protection groups as required. Process (E) is analogous to Process (D) and may be carried under the same conditions.

Process g) may be conveniently carried out by chemical reduction for example using a trialkylsilane, e.g triethylsilane, under acidic conditions (e.g trifluoroacetic acid) and an inert solvent e.g dichloromethane to give predominantly the trans configuration of bridgehead hydrogens. Reduction via catalytic hydrogenation, e.g using palladium on carbon, gives predominantly the cis configuration of bridgehead hydrogens.

With regard to processes (h) and (F) conversions may be carried out by known means, e.g an alcohol may be formed from an ester substitutent by reduction using lithium borohydride with heating if desired in the presence of an inert solvent, e.g tetrahydrofuran. Under more vigorous conditions, e.g reflux, bridgehead double bonds may likewise be reduced. Process (h) also includes conversion of substituents on $R^4$ and/or $R^3$ when each represents an aromatic radical. Such methods are well known in the art. For example an alkoxy substituent can be convened to hydroxy using boron tribromide. An arylmethoxy substituent can be hydrogenated to give hydroxy. Nitro substituents can be reduced to amino substituents. Amino substituents can be acylated e.g using an acyl halide to give acylamino, or sulphonylated to give a sulphonamide, or alkylated to give an alkylamino, e.g by reductive alkylation.

With regard to process (i) the reaction may be conveniently carried out under conditions suitable for the Wolff-Kishner (Organic Reactions IV p 373 (1948) and Merck Index 7th Edn. 1960 p 1479) to give the compound of formula IA wherein Y is $CH_2$.

Processes (j) and (G) may be conveniently carried out using a reducing agent, e.g a trialkylsilane under acidic conditions such as trifluoroacetic acid. As a by-product hydroxy substitution can also occur to give a compound of formula IA wherein $R^8$ is hydroxy. Process (G) may also be carried out using catalytic hydrogenation, e.g using palladium on carbon in an inert solvent or by chemical reduction.

Process (k) may be carried out by catalytic hydrogenation e.g using Pearlman's catalyst ($Pd(OH)_2$ on carbon) under acidic conditions such as glacial acetic acid.

Process (l) may conveniently be carried out in two steps by taking the anion of formula (S), (e.g formed by adding lithium tetramethylpiperidine to the appropriate compound of formula IA) and reacting the anion with an electrophile of formula $halCH_2O(CH_2)_2Si(alkyl)_3$ to give a trialkylsilylethoxy derivative and hydrolysing the product, e.g using boron trifluoride etherate in dichloromethane.

As mentioned above standard resolution techniques can be used in process (m) to isolate enantiomeric forms of the compounds of formula I and IA. Such techniques are well known in the art. Where necessary in the reactions described herein protecting groups may be used to protect reactive sites during a reaction and removed thereafter. Once a compound of formula I or IA is prepared containing a reactive substituent group or site, e.g an alkanoyloxy substituent, or an acidic proton, then such compounds may be converted to a different compound of formula I, e.g hydrolysed to give corresponding hydroxy compounds of formula I. Compounds of formula I having an acidic proton may be metallated e.g. lithiated, and reacted with an electrophile e.g R' Br or R" Br to give other compounds of formula I. Similarly compounds of formula I containing a hydroxy group may be acylated, e.g using alkanoyl halides to give corresponding alkanoyl compounds of formula I. Similarly when an alkoxy substituent is present then such compounds may be dealkylated using standard procedures to give corresponding hydroxy compounds of formula I. When $R^4$ is hydrogen the nitrogen may be alkylated or aralkylated e.g. by treating with sodium hydride and reacting the anion with a halide of formula $R^a$, $R^b$ $R^c$ to give compounds of formula I and Ia wherein $R^4$ is other than hydrogen Accordingly compounds of formula I may also be intermediates for other compounds of formula I.

As discussed above starting materials for the processes described herein are known compounds or can be made by analogous methods for known compounds. For example compounds of formula (VI) can be prepared by Michael addition to an enamine (formed from a cyclic ketone) as shown in Reaction Scheme I below:

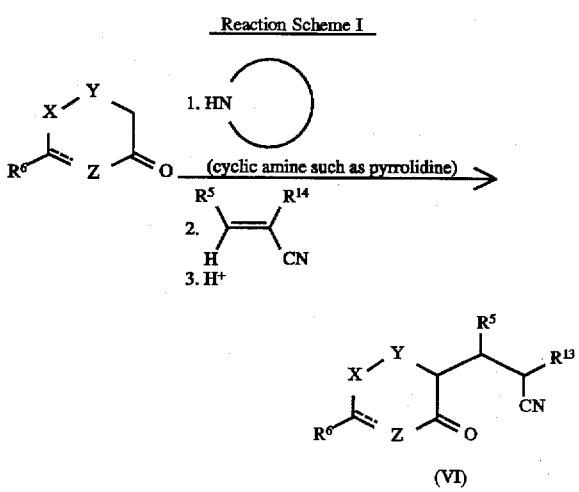

(VI)

Similarly a compound of formula (VII) can be prepared by the above reaction but using an acrylic ester of formula:

(XIII)

instead of an acrylonitrile.

Compounds of formula VIII used in process (c) can be prepared by reacting a compound (VII) as defined hereinabove with an amine of formula $R^4NH_2$ to give an imine and reducing the imine.

Suitable methods for reducing the imine are catalytic hydrogenation, e.g using Raney nickel and hydrogen, or using a reducing agent such as an alkali metal in borohydride (e.g sodium borohydride or sodium cyanoborohydride). In the case of the latter reducing agents the reduction may be carried out simultaneously with imine formation so that the net effect is reductive amination. Raney nickel hydrogenation of 2-substituted cyclohexylimines generally gives a cis-reduced product, i.e where the hydrogen in the 1 and 2 position are both cis configuration. Borohydride reduction on the other hand gives a mixture of cis and trans configuration of hydrogens in the 1 and 2 positions.

Compounds of formula (IX) may be prepared by one of the following:

i) reacting a compound of formula:

(XV)

compound of formula (XV) with a compound of formula:

(XVII)

wherein $COOR^{12}$ is an ester group; to give a compound formula (IX) wherein B has formula (v), and the bridgehead double bond is present and $R^{14}$ is as defined above, i.e a compound having formula:

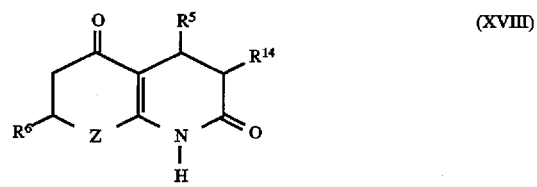

(XVIII)

When $R^{14}$ is hydrogen it can be converted to other values of $R^2$ by reacting a suitably protected (e.g. 1-NH and 5-oxo protected) anionic form with an appropriate electrophile, e.g $ClCOO(C_1-C_6$ alkyl) or $ClCH_2OCH_2CH_2SiMe_3$ which forms are or can be converted to the required $R^2$ group.

Protecting groups for the 5-oxo group include ketals or dithiolanes. The nitrogen in the 1-position may be protected by $-SiMe_2{}^tBu$. Different $R^4$ groups can be introduced by alkylation of the 1-sodio salt.

Compounds of formula (X) can be prepared by (i) reacting a ketal protected compound of formula:

(XIX)

with a compound of formula (XX):

(XX)

where Y, Z, $R^2$, $R^5$ and $R^6$ are as defined above, or $R^2$ is convertible thereto, to give a corresponding compound of formula (X) wherein and the bridgehead double bond is present followed by deprotection to remove the ketal.

Compounds of formula (XII) may be prepared hydrolysing a compound of formula:

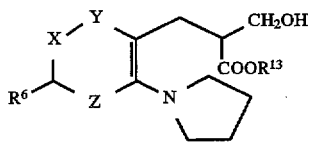

where X, Y and Z are as defined above and $R^{13}$ is alkyl, e.g methyl under acidic conditions e.g glacial acetic acid.

This invention also provides novel intermediates for preparing the active compounds of this invention, and processes for preparing them. In particular this invention provides compound of formula II, III, IV, VI and VII as hereinbefore defined and processes for preparing them.

The compounds of this invention may be obtained in free base form or as acid addition salts as desired. Examples of such salts include salts with pharmaceutically acceptable organic or inorganic acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-toluene sulphonic acids.

When acidic substituents are present it is also possible to form salts by treatment with bases, to give for example alkali metals (such as sodium) or ammonium salts. Such salts of the compounds of formula I are included within the scope of this invention.

When basic substituents are present then quaternary ammonium salts may be formed by quaternizing with an alkylating agent such as alkyl or aralkyl halides.

This invention also provides pharmaceutical compositions comprising a compound of formula I or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table disintegrating agents; it can also be encapsulating material. In powders the carrier is a finely divided solid which is in admixture with the the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included. Sterile liquid form compositions include sterile solutions, suspensions, emulsions, syrups and elixirs. The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally. Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound and the disease to be treated. For certain of the above mentioned conditions it is clear that the compounds may be used prophylactically as well as for the alleviation of acute symptoms. References herein to "treatment" or the like are to be understood to include such prophylactic treatment, as well as treatment of acute conditions.

The following Examples illustrate the invention and methods for preparing compounds of the invention. In the Examples relative configurations of optical centres are denoted using the R,S notation. As used herein (±)–(3RS, 4aRS,6SR,8aSR) means a racemic mixture of the 3R,4aR, 6S,8aS and 3S,4aS,6R,8aR enantiomers. Where the optical rotation is known but the absolute configuration is not then the following is used: (+)–(3R,4aR,6S,8aS) or (3S,4aS,6R, 8aR) for example.

EXAMPLE 1

3,4,5,6,7,8-Hexahydro-6-((4-methoxyphenyl) methyl)-3-methylquinolin-2[1H]-one a) 2-(2-Cyanopropyl)-4-(4-methoxybenzyl) cyclohexanone 1,4-Dioxospiro[4,5]decan-8-one (45.6 g) was added to a mixture of 4-methoxybenzyl triphenylphosphonium bromide (127.3 g) and epichlorohydrin (100 ml) in toluene (1500 ml) and heated at reflux under a nitrogen atmosphere for 36 hours. The solvent was evaporated under reduced pressure and the residue was extracted into hexane. The hexane solution was evaporated under reduced pressure and the residue distilled at 240° C./1 mmHg to give 8-(4-methoxybenzylidine)-1,4-dioxaspiro[4,5]decane, (19 g). 8-(4-Methoxybenzylidene)-1,4-dioxaspiro[4,5]decane (16.5 g) was dissolved in hexane (300 ml) and hydrogenated at atmospheric pressure in the presence of 10% Pd/C (3.5 g).

When hydrogen uptake had ended the reaction mixture was filtered through kieselguhr to give, after evaporation of the solvent 8-(4-methoxybenzyl)-1,4-dioxaspiro[4,5] decane, (16.5 g).

8-(4-Methoxybenzyl)-1,4-dioxaspiro[4,5]decane (47 g) was added to 80% aqueous acetic acid (150 ml) at 65° C. and was left to stir for 2½ hours after which time the solvent was evaporated under reduced pressure. The residue was dissolved in ethyl acetate and washed with water. The organic phase was dried (MgSO₄) and evaporated under reduced pressure to give after distillation at 180° C./0.04 mmHg 4-(4-methoxybenzyl)-cyclohexanone, (40 g).

4-(4-Methoxybenzyl)cyclohexanone (10.25 g) was heated at reflux in toluene (500 ml) containing pyrrolidine (16 ml) and toluene-4-sulphonic acid (0.1 g). Water in the condensate was collected in a Dean and Stark apparatus. After 2 hours the solvent was removed by distillation until the reaction volume was approximately 100 ml. Ethanol (250 ml) and methacrylonitrile (20 ml) was added and the mixture heated at reflux for 16 hours, after which the solvent was evaporated under reduced pressure. The residue was dissolved in ethyl acetate and washed with 1M citric acid and saturated sodium carbonate solution. The organic phase was dried (MgSO$_4$) and evaporated under reduced pressure to give 2-(2-cyanopropyl)-4-(4-methoxybenzyl) cyclohexanone (10.2 g).

b) 3,4,5,6,7,8-Hexahydro-6-((4-methoxyphenyl)methyl)-3-methylquinolin-2[1H]-one 2-(2-Cyanopropyl)-4-(4-methoxybenzyl)cyclohexanone (1.5 g) was added to glacial acetic acid (20 ml) containing 45% w/v hydrogen bromide in acetic acid (5 ml) and the mixture was left to stir for 2½ hours. The solvent was removed under reduced pressure, the residue was suspended in water and filtered to give the title compound on recrystallisation (0.5 g) mp 182°–184° C.

Analysis: $C_{18}H_{23}NO_2$ requires: C, 75.6; H, 8.15; N, 4.9%
Found: C, 76.0; H, 7.8; N, 4.9%.

EXAMPLE 2

3,4,4a,5,6,7,8,8a-Octahydro-6-((4-methoxyphenyl) methyl)-3-methylquinolin-2[1H]-one 3,4,5,6,7,8-Hexahydro-6-((4-methoxyphenyl)methyl)-3-methylquinolin-2[1H]-one (0.25 g) prepared according to Example 1, was suspended in triethylsilane (0.5 ml) and trifluoroacetic acid (0.5 ml) was added. The mixture was stirred for 30 minutes and then evaporated under reduced pressure. The residue was dissolved in chloroform and washed with saturated sodium carbonate solution and then with brine. The organic solution was dried (MgSO$_4$) and evaporated to give the crude product (0.28 g), which was combined with a further batch 0.38 g. The crude product was purified by crystallisation from ethyl acetate/cyclohexane to give the title compound (0.2 g) m.p. 180°–208° C.

Analysis: $C_{18}H_{25}NO_2$ requires: C, 75.2; H, 8.8; N, 4.9%
Found: C, 75.1; H, 9.0; N, 4.8%.

EXAMPLE 3

3,4,5,6,7,8-Hexahydro-6-((4-hydroxyphenyl)methyl)-3-methylquinolin-2[1H]-one 3,4,5,6,7,8-Hexahydro-6-((4-methoxyphenyl)methyl)-3-methylquinolin-2[1H]-one (2.85 g) prepared according to Example 1 (2.85 g) was suspended in dichloromethane (5 ml) and cooled with ice and boron tribromide (3.3 ml) was added. The mixture was left to stir until tlc (SiO$_2$/chloroform) showed no starting material remained and then the mixture was quenched by slow addition of water (10 ml). The reaction mixture was further diluted with water and the resulting solid was isolated by filtration. The solid was dissolved in methanol (100 ml) and concentrated HCl (1 ml) was added. The methanol was removed under reduced pressure and the procedure repeated three times. The solid was suspended in ethyl acetate, filtered and washed with ether to give the hemihydrate of the title compound (2.22 g), mp.230°–235° C.

Analysis: $C_{17}H_{21}NO_2 \cdot$ ½ $H_2O$ requires: C, 72.8; H, 7.9; N, 5.0%
Found: C, 73.1; H, 7.85; N, 5.3%.

EXAMPLE 4

3,4,4a,5,6,7,8,8a-Octahydro-6-((4-hydroxyphenyl) methyl)-3-methylquinolin-2[1H]-one 3,4,5,6,7,8-Hexahydro-6-((4-hydroxyphenyl)methyl)-3-methylquinolin-2[1H]-one (1.5 g) was suspended in triethylsilane (3 ml) and TFA (3 ml) was added. The mixture was left to stir for 30 minutes then was evaporated under reduced pressure. The residue was dissolved in chloroform and washed with sodium bicarbonate solution, dried (MgSO$_4$) and evaporated. The residue was recrystallised from isopropanol to give the title compound (0.6 g,) mp. 217°–223° C.

Analysis: $C_{17}H_{23}NO_2$ requires: C, 74.7; H, 8.5; N, 5.1%.
Found: C, 74.5; H, 8.3; N, 5.2%.

EXAMPLE 5

Ethyl 3,4,5,6,7,8-hexahydro-6-((4-methoxyphenyl) methyl)quinolin-2[1H]-one-3-carboxylate a) 4-((4-Methoxybenzyl)cyctohexanone (3.87 g, prepared as described in Example 1a) was dissolved in toluene (150 ml) containing morpholine (7.8 ml) and toluene-p-sulphonic acid (0.1 g) and the mixture was heated at reflux. Water generated during the reaction was collected using a Dean and Stark trap. After 18 hours the reaction mixture was evaporated under reduced pressure and when all the morpholine had been removed, the residue was redissolved in toluene (100 ml) and cooled to ice temperature. To this solution was added ethyl 2-cyanoacrylate (5 g) with rapid stirring. After 18 hours the reaction mixture was evaporated under reduced pressure and the residue dissolved in 85% aqueous acetic acid. After 30 minutes the reaction mixture was diluted with water and extracted into ethyl acetate. The organic phase was dried (MgSO$_4$) and evaporated under reduced pressure. The residue was purified by chromatography, first on silica using ethyl acetate as eluent and then on silica using dichloromethane as eluent. The solvent was evaporated under reduced pressure to give 2-cyano-3-[3-(4-methoxyphenyl)methyl-6-oxocyclohexanyl]propanoic acid ethyl ester (5.14 g. 83%).

b) 2-Cyano-3-(3-(4-methoxyphenyl)methyl-6-oxocyclohexanyl)propanoic acid ethyl ester (2.43 g) was added to 15% w/v solution of HBr in acetic acid at 5° C. and stirred for 30 minutes. The reaction mixture was evaporated under reduced pressure and washed with saturated sodium carbonate solution. The mixture was extracted into ethyl acetate and the organic phase dried (MgSO$_4$) and evaporated. The residue was diluted with diethyl ether and allowed to crystallise to give the title compound (0.5 g) mp. 143°–145° C.

Analysis: $C_{20}H_{25}NO_4$ requires C, 69.9; H, 7.3; N, 4.1;
Found: C, 69.9; H, 7.55;N, 4.0%.

EXAMPLE 6

Ethyl 3,4,4a,5,6,7,8,8a-octahydro-6-((4-methoxyphenyl)methyl)quinolin-2[1H]-one-3-carboxylate Ethyl 3,4,5,6,7,8-hexahydro-6-((4-methoxyphenyl) methylquinolin-2[1H]-one-3-carboxylate (0.35 g) (prepared as in Example 5) was dissolved in CH$_2$Cl$_2$ (1 ml) and triethylsilane (1.5 ml) was added. The solution was cooled with ice. TFA (1.5 ml) was added and the mixture was left to stir 1.5 hours. The reaction mixture was evaporated under reduced pressure and the residue dissolved in chloroform. The chloroform solution was washed with saturated sodium carbonate solution, dried (MgSO$_4$) and evaporated. The residue was suspended in ether, filtered and the solid obtained was recrystallised from ethyl acetate to give the title compound (0.14 g) mp 142°–144° C.

Analysis: C$_{20}$H$_{27}$NO$_4$ requires: C, 69.55; H, 7.9; N, 4.1%
Found: C, 69.5; H, 8.3; N, 3.9%.

EXAMPLE 7

3,4,4a,5,6,7,8,8a-Octahydro-3-hydroxymethyl-6-((4-methoxyphenyl)methyl)quinolin-2[1H]-one Ethyl 3,4,4a,5,6,7,8,8a-octahydro-6-(4-methoxyphenyl)methyl-quinolin-2[1H]-one-3-carboxylate (1 g) (prepared according to Example 6) was mixed with 2M lithium borohydride solution in THF (15 ml) and heated at reflux. After 4 hours the reaction mixture was quenched by addition of water. The reaction mixture was partitioned between water and dichloromethane and the organic layer was washed with 2M HCl, then with saturated sodium carbonate solution, dried (MgSO$_4$) and evaporated. The residue was recrystallised from methanol to give the title compound (0.092 g) mp 193°–200° C.

Analysis: C$_{18}$H$_{25}$NO$_3$ requires: C, 71.3; H, 8.3; N, 4.6%
Found: C, 71.0; H, 8.6; N, 4.5%.

EXAMPLE 8

3,4,4a,5,6,7,8,8a-Octahydro-3-hydroxymethyl-6-((4-hydroxyphenyl)-methyl)quinolin-2[1H]-one 3,4,4a,5,6,7,8,8a,-Octahydro-3-hydroxymethyl-6-((4-methoxyphenyl)methyl)-quinolin-2[1H]-one (0.26 g) (prepared according to Example 7) was dissolved in dichloromethane and cooled to ice temperature. 1M Boron tribromide in dichloromethane (4.3 ml) was added and the mixture was left 2 hours after which a further 75 ml of dichloromethane was added. After a further 1 hour the reaction mixture was quenched by addition of water (2 ml) and evaporated under reduced pressure. The residue was dissolved in methanol (100 ml) containing conc. HCl (1 ml) and the methanol was evaporated under reduced pressure; the process being repeated three time. The residue was basified with saturated sodium bicarbonate solutions and was extracted into chloform. The chloroform layer was dried (MgSO$_4$) and evaporated. The residue was recrystallised from isopropanol/diisopropyl ether to give the title compound (0.035 g) mp 126°–128° C.

Analysis: C$_{17}$H$_{23}$NO$_3$.¾H$_2$O.½Me$_2$CHOH requires: C, 66.8; H, 8.8; N, 3.9
Found: C, 66.7; H, 8.6; N, 4.2%.

EXAMPLE 9

3,4,5,6,7,8-Hexahydro-6-((4-methoxyphenyl) methyl)quinolin-2[1H]-one a) 4-(4-Methoxybenzyl)cyclohexanone (112 g) (prepared as described in Example 1 (a)) pyrrolidine (100 g), and p-toluene sulphonic acid (0.3 g) were dissolved in toluene (1.5l) and heated to reflux under argon with Dean-Stark water separation. When water ceased to separate (ca 2.5 hours) the remaining pyrrolidine and solvent were evaporated off and the residue dissolved in absolute ethanol (1 litre). The product was treated with acrylonitrile (27.2 g) in ethanol (30 ml). After 2 hours at reflux the reaction was left to cool and then concentrated in vacuo. The residue was treated with water (1 litre) and acetic acid (200 ml). After stirring for 2 hours the mixture was extracted into diethyl ether and the organic phase dried (Na$_2$SO$_4$) and concentrated to yield 2-(2-cyanoethyl)-4-(4-methoxyphenyl)cyclohexanone as an oil (140 g).

b) 2-(2-Cyanoethyl)-4-(4-methoxyphenyl)cyclohexanone (104 g) from step (a) above in acetic acid (200 ml) was added dropwise to a stirred solution of 45% HBr in acetic acid (150 ml) keeping the temperature below 10° C. Immediately after the addition was completed, the reaction mixture was poured onto ice water and the product extracted into t-butylmethyl ether, from which the product crystallised on standing. The mother liquors were combined with further ethyl acetate extractions of the aqueous phase, and were chromatographed using diisopropyl ether/dichloromethane (10:3) as eluent on SiO$_2$. The less pure fractions from the column were combined and concentrated to yield a solid. After trituration of this solid with diethyl ether the product batches were combined and recrystallisation from acetonitrile to give the title compound. (88.5 g) mp 176°–7° C.

Analysis: C$_{17}$H$_{21}$NO$_2$ requires: C, 75.3; H, 7.7; N, 5.2%
Found: C, 75.4; H, 7.9; N, 5.1%.

EXAMPLE 10

(±)-(3RS,4aRS,6SR,8aSR)-3,4,4a,5,6,7,8,8a-Octahydro-3-hydroxymethyl-6-((4-methoxyphenyl) methyl)quinolin-2[1H]-one In a manner analogous to Example 6, but using THF solvent instead of CH$_2$Cl$_2$, ethyl 3,4,4a,5,6,7,8,8a-octahydro-6-((4-methoxyphenyl)methyl)quinolin-2[1H]-one-3-carboxylate was prepared as a 60:40 w/w mixture of (±)-(3RS,4aSR,6RS,8aRS) to (±)-(3SR,4aSR,6RS,8aRS) isomers). This product was suspended in THF (20 ml) at 0° C. and an ice cold solution of 1M lithium borohydride in THF (13.1 ml) was added. The mixture was left to stir 5½ hours at 0° C. and then was added to methanolic hydrogen chloride (120 ml). The acidic solution was left to stand 18 hours and was then evaporated. The residue was dissolved in chloroform and washed with saturated sodium carbonate solution, water and then brine. The organic solution was dried (MgSO$_4$), evaporated and the residual oil was left to stir in hexane containing a small quantity of ethyl acetate for 3 days. The resin obtained was purified by repeated chromatography on a 4 mm "Chromatotron" plate. The early running fractions were combined to give 0.2 g of the title compound. This was recrystallised from ethyl acetate mp 205°–209° C.

Analysis: C$_{18}$H$_{25}$NO$_3$ requires: C, 71.3; H, 8.3; N, 4.6%
Found: C, 70.9; H, 8.3; N, 4.45%.

EXAMPLE 11

(±)-(3RS,4aSR,6RS,8aRS)-3,4,4,4a,5,6,7,8,8a-Octahydro-3-hydroxymethyl-6-((4-methoxyphenyl) methyl)quinolin-2[1H]one The later running fractions from Example 10 were combined to give 0.11 g of the (±)-(3RS,4aSR,6RS,8aRS) isomer. This was recrystallised from methanol to give the title compound as the quarterhydrate mp 196°–199° C.

Analysis: C$_{18}$H$_{25}$NO$_3$. ¼ H$_2$O requires: C, 70.1; H, 8.25; N, 4.4%
Found: C, 70.2; H, 8.4: N, 4.6%.

EXAMPLE 12

(±)-(3SR,4aRS,6SR,8aRS)-3,4,4a,5,6,7,8,8a-Octahydro-3-hydroxymethyl-6-((4-methoxyphenyl) methyl)quinolin-2[1H]-one The procedure of Example 10 was repeated and the title compound was also obtained by chromatography on a 4 mm "Chromatotron" plate.

Analysis: $C_{18}H_{25}NO_3$ requires: C, 71.3; H, 8.3; N, 4.6%
Found: C, 71.0; H, 8.3; N, 4.6%

EXAMPLE 13

(±)-(4aRS,6RS,8aSR)-3,4,4a,5,6,7,8,8a-Octahydro-6-((4-methoxyphenyl)methyl)quinolin-2[1H]-one 3,4,5,6,7,8-Hexahydro-6-((4-methoxyphenyl)methyl) quinolin-2[1H]-one (2.5 g) in methanol (100 ml) containing 5 drops of concentrated HCl was hydrogenated over a Pd/C catalyst at 50 psi and 50° C. for 4 days. The catalyst was filtered off and the filtrate evaporated to give 2.4 g of a product. This was purified initially on a silica column using t-butylmethyl ether to remove starting material (Rf 0.2). Product remaining on the baseline was eluted with methanol, evaporated and the resultant solid purified by chromatography on silica using ethyl acetate as eluent. The major fraction was isolated and recrystallised from diethyl ether to give the title compound as the ¼ hydrate, mp 161°–163° C.

Analysis: $C_{17}H_{23}NO_2 \cdot \frac{1}{4}H_2O$ requires: C, 73.5; H, 8.5; N, 5.0%
Found: C, 73.3; H, 8.3; N, 4.9%

EXAMPLE 14

(±)-(4aRS,6RS,8aRS)-3,4,4a,5,6,7,8,8a-Octahydro-6-((4-methoxyphenyl)methyl)-quinolin-2[1H]-one 3,4,5,6,7,8-Hexahydro-6-((4-methoxyphenyl)methyl) quinolin-2[1H]-one (1.5 g) (prepared according to Example 9) was dissolved in dichloromethane (50 ml) and cooled to 0° C. Triethylsilane (0.9 ml and trifluoroacetic acid (5 ml) were added and the mixture was stirred for 2 hours. The reaction mixture was then evaporated under reduced pressure, crystallised by addition of ether and recrystallised from acetonitrile to give the title compound (0.7 g), mp 194°–196° C.

Analysis: $C_{17}H_{23}NO_2$ requires: C,74.7; H, 8.5; N, 5.1%
Found: C,75.0; H, 8.4; N, 5.1%.

EXAMPLE 15

(±)-(4aRS,6RS,8aRS)-3,4,4,5,6,7,8,8a Octahydro-6-((4-hydroxyphenyl)-methyl)quinolin-2[1H]-one (±)-(4aRS,6RS,8aRS)-3,4,4a,5,6,7,8,8a-Octahydro-6-((4-methoxyphenyl)-methyl)quinolin-2[1H]-one (0.5 g) (prepared according to Example 14) was dissolved in DMF (2.5 ml) and added in DMF (1 ml) to propanethiol (0.35 ml) and 4 ml of 1M potassium t-butoxide (in THF). The THF solvent was evaporated under a stream of argon and the reaction mixture heated at reflux for 18 hours. The reaction mixture was then acidified with hydrochloric acid and the aqueous solution extracted with ethyl acetate. A solid precipitated during the ethyl acetate extraction and was isolated by filtration to give the crude product (0.12 g). Recrystallisation from methanol gave the title compound (0.11 g) mp 277°–279° C.

Analysis: $C_{16}H_{21}NO_2 \cdot \frac{1}{4}H_2O$ requires: C, 72.8; H, 8.2; N, 5.3%
Found: C, 72.5; H, 8.0; N, 5.3%.

EXAMPLE 16

3,4,5,6,7,8-Hexahydro-6-((4-methoxyphenyl) methyl)quinolin-2[1H]-one-3-carbonitrile 2-Cyano-3-[3-(4-methoxyphenyl)methyl-6-oxocyclohexanyl]propanoic acid ethyl ester (1 g) (prepared as described in Example 5(a)) in methanol (10 ml) was treated with ammonium acetate (2.2 g) and left to stir at room temperature for 2 hours. The reaction mixture was diluted with water and a solid crystallised out. The solid was mixed with water and methanol, and the methanol removed under reduced pressure. The mixture was extracted into ethyl acetate, dried ($MgSO_4$), and solvent evaporated to give the title compound as the quarterhydrate, mp 158°–9° C.

Analysis: $C_{18}H20N_2O_2 \cdot \frac{1}{4}H_2O$ requires: C, 71.9; H, 6.9; N, 9.3%
Found: C, 71.8; H, 6.6; N, 9.3%.

EXAMPLE 17

3,4,5,6,7,8-Hexahydro-3-hydroxymethyl-6-((4-methoxyphenyl)methyl)quinolin-2[1H]-one a) Paraformaldehyde (200 g) in $H_2O$ (300 ml) was heated at reflux and treated with conc. $H_2SO_4$ (1 ml). The reaction was refluxed for 3 hours, cooled and added to triethylphosphonoacetate (255 g). The mixture was stirred vigorously at room temperature whilst adding a saturated solution of potassium carbonate (280 g). After 18 hours the reaction mixture was treated with saturated $NH_4Cl$ solution (375 ml), extracted into diethyl ether, dried ($Na_2SO_4$) and concentrated in vacuo. The resulting ethyl 2-hydroxymethylacrylate was distilled at 80° C. under 5 mmHg and used in the following step.

b) 4-(4-Methoxyphenyl)methylcyclohexanone (18 g) in toluene (500 ml) was treated with pyrrolidine (9 g) and a catalytic amount of p-toluenesulphonic acid. The reaction mixture was heated at reflux for 3 hours, with Dean-Stark water separation. The solution was then concentrated in vacuo, toluene was added and the solution concentrated again to remove remaining traces of pyrrolidine. The residual oil was dissolved in absolute ethanol (250 ml) and treated with ethyl 2-hydroxymethylacrylate (12.6 g) from step a). The reaction mixture was stirred at room temperature for 48 hours and brought to pH 5–6 with 20% aqueous acetic acid. After stirring for ½ hour the mixture was concentrated in vacuo and partitioned between water and ethyl acetate. The organic layer was dried ($Na_2SO_4$) and chromatographed on $SiO_2$ using diisopropyl ether as solvent to give 3,4,4a,5,6,7,8,8a-octahydro-3-ethoxycarbonyl-8a-hydroxy-6-(4-methoxyphenyl)methyl-2H-benzo[b]pyran (21 g).

c) 3,4,4a,5,6,7,8,8a-Octahydro-3-ethoxycarbonyl-8a-hydroxy-6-(4-methoxyphenyl)methyl-2H-benzo[b]pyran (21 g) in methanol (100 ml) was heated under reflux with ammonium acetate (40 g) for 18 hours. The mixture was evaporated to dryness and the residue partitioned between water and chloroform. The chloroform extract was dried ($Na_2SO_4$), treated with charcoal and evaporated to give an oil. This was crystallised from ethylacetate to give the title compound mp 165°–168° C.

Analysis: $C_{18}H23NO_3$ requires: C, 71.8; H, 7.6; N, 4.6%
Found: C, 71.7; H, 7.7; N, 4.5%.

EXAMPLE 18

(−)-(1S,3'R,4a'R,6'S,8a'S)(3',4',4a',5',6',7',8',8a')-Octahydro-6'-((4'-methoxyphenyl)methylquinolin-2'[1'H]-on-3'-yl)methyl(1-(1-naphthalenyl)ethyl) carbamate (±)-(3RS,4aRS,6SR,8aSR)-3,4,4a,5,6,7,8,8a-Octahydro-3-hydroxymethyl-6-((4-methoxyphenyl)methyl)quinolin-2 [1H]-one (0.2 g,prepared according to Example 10) was suspended in benzene (10 ml) containing N,N-dimethylethanolamine (0.1 ml) and (S)-(+)-1-(1-naphthyl)ethylisocyanate (0.15 ml). After heating at reflux 4½ hours, the reaction mixture was evaporated under reduced pressure and the residue purified by chromatography using a 1 mm "Chromatotron" plate with ethyl acetate as eluent.

The band corresponding to Rf 0.4 (SiO$_2$/ethyl acetate) yielded on evaporation the title compound, 0.11 g, mp=149°–151°,[α]$_D^{27}$=–12° (1% CHCl$_3$).

Analysis C$_{31}$H$_{36}$N$_2$O$_4$ requires: C, 74.4; H, 7.25; N, 5.6%
Found: C, 74.5; H, 7.3; N, 5.5%.

EXAMPLE 19

(+)-(1S,3'S,4a'S,6'R,8a'R)(3',4',4a',5',6',7',8',8a'-Octahydro-6'-((4'-methoxyphenyl)methylquinolin-2'-[1'H]-on-3'-yl)methyl(1-(1-naphthalenyl)ethyl)carbamate The band corresponding to Rf 0.32 (SiO$_2$/ethyl acetate) from Example 18 yielded on evaporation the (+) isomer of the title compound, 0.09 g, mp=200°–204° C., [α]$_D^{26}$=+56° (1% CHCl$_3$).

Analysis C$_{31}$H$_{36}$N$_2$O$_4$ requires C, 74.4; H, 7.25; N, 5.6%
Found C, 74.1; H, 7.5; H, 5.4%.

EXAMPLE 20

(+)-(3S,4aS,6R,8aR)-3,4,4a,5,6,7,8a-Octahydro-3-hydroxymethyl-1-6-4-methoxyphenyl)methylquinolin-2[1H]-one (+)-(1S,3'R,4a'R,6'R,8a'S)(3',4',4a',5',6',7',8',8a')-Octahydro-6'-((4'-methoxyphenyl)methylquinolin-2'[1'H]-on-3'-yl)methyl(1-(1-naphthalenyl)-ethyl)carbamate (0.16 g) from Example 19 in toluene (25 ml) was treated with triethylamine (0.045 ml), followed by trichlorosilane (0.035 ml) and was stirred at room temperature for 24 hours. More triethylamine (0.045 ml) and trichlorosilane (0.035 ml) were added and the mixture stirred at room temperature for a further 3 hours. Aqueous ammonia (20 ml, 80:20) was added and the mixture stirred for 4 hours. The solution was filtered and the organic phase dried (MgSO$_4$) and evaporated. The resulting gum was purified by chromatography on silica using ethyl acetate as eluent to give the title product (16 mg), mp 167°–169° C., [α]$_D^{26}$=27° (1% CHCl$_3$).

Analysis: C$_{18}$H$_{25}$NO$_3$ requires: C, 71.3; H, 8.3; N, 4.6.
Found: C, 70.8; H, 8.5; N, 4.3%.

EXAMPLE 21

(±)-(3SR,4aRS,6SR,8aRS)-3,4,4a,5,6,7,8,8a-Octahydro-3-hydroxymethyl-6-((4-methoxyhenl)methyl)quinolin-2[1H]-one 3,4,5,6,7,8-Hexahydro-3-hydroxymethyl-6-((4-methoxyphenyl)methyl)quinolin-2[1H]-one (6.75 g) (prepared according to Example 17) was suspended in triethylsilane (35 ml) and TFA (17.25) ml was added with rapid stirring. When tlc (SiO$_2$/EtOAc) showed no starting material remained, the stirring was stopped and the reaction mixture separated into two layers. The lower (TFA) layer was added to a saturated solution of sodium carbonate and this organic solution was extracted into dichloromethane, dried (MgSO$_4$) and evaporated. The residue (9.4 g) was purified in several fractions to give 3,4,4a,5,6,7,8,8a-octahydro-3-hydroxymethyl-6-((4-methoxyphenyl)methyl)quinolin-2[1H]-one (mixed isomers 4.58 g). This product was purified by chromatography on a "Dynamax" 60A Si 21×250 mm column using 0.25% NH$_4$OH, 1.8% MeOH in dichloromethane as mobile phase. A flow rate of 21.6 ml/min was used and injections of 10 ml of 10 mg/ml of product in mobile phase were made. The material eluting at 20.1 minutes was collected and recrystallised from ethyl acetate to give the title compound (0.2 g) mp 196°–197° C.

Analysis: C$_{18}$H$_{25}$NO$_3$ requires: C, 71.3; H, 8.3; N, 4.6%
Found: C, 71.0; H, 8.3; N, 4.6%.

(a) Also obtained from the abovementioned chromatographic separation was (±)-(3RS,4aRS,6SR,8aSR)-3,4,4a,5,6,7,8,8a-octahydro-3-hydroxymethyl-6-((4-methoxyphenyl)methyl)quinolin-2[1H]-one, eluting at 22.1 minutes and (±)-(3SR,4aRS,6SR,8aSR)-3,4,4a,5,6,7,8,8a-octahydro-3-hydroxymethyl-6-(4-methoxyphenyl)methyl)quinolin-2[1H]-one eluting at 24.9 minutes.

EXAMPLE 22

(+)-(3R,4aS,6R,8aS) or (3S,4aR,6S,8aR)-3,4,4a,5,6,7,8,8a-Octahydro-3-hydroxymethyl-6-((4-methoxyphenyl)methyl)quinolin-2[1H]-one (±)-(3SR,4aRS,6SR,8aRS)-3,4,4a,5,6,7,8,8a-Octahydro-3-hydroxymethyl-6-((4-methoxyphenyl)methyl)quinolin-2-[1H]-one (0.19 g) (prepared according to Example 21) was separated by chromatography using a "Dynamax" C18 21×290 mm column with 2% beta-cyclodextrin, 0.1% triethylammonium acetate and 15% acetonitrile in water as mobile phase. The flow rate was 17.5 ml/min and 12 mg injections were made. Fractions eluting at 25.2 minutes and 30.6 minutes were collected. The fraction eluting at 25.2 minutes was evaporated to dryness and the solid obtained was extracted with chloroform using a soxlet apparatus. The chloroform solution was evaporated to dryness and the residue was purified by chromatography on a "Dynamax" 60 A Si 21×290 mm column using 0.25% NH$_4$OH and 1.8% MeOH in dichloromethane as mobile phase. A flow rate of 21.6 ml/mins was used. The material eluting at 20.1 minutes was collected and evaporated to yield the title compound, (40 mg), [α]$_D^{26}$=+55° (1%, CHCl$_3$), mp 208°–210° C.

Analysis: C$_{18}$H$_{25}$NO$_3$·⅓H$_2$O requires C, 70.0; H, 8.4; N, 4.5%
Found: C, 69.8; H, 8.4; N, 4.3%.

EXAMPLE 23

(–)-(3R,4aS,6R,8aS) or (3S,4aR,6S,8aR)-3,4,4a,5,6,7,8,8a-Octahydro-3-hydroxymethyl-6-(4-methoxypheny)methyl)quinol-2[1H]-one The fraction eluting at 30.6 mins from Example 22 was isolated and purified in the same manner as described in Example 22 to give the title compound (10 mg) purity ca. 95%, [α]$_D^{26}$=–35°(1%,CHCl$_3$).

EXAMPLE 24

(–)-3R,4aR,6S,8aS)-3,4,4a,5,6,7,8,8a-Octahydro-3-hydroxymethyl-6-((4-methoxyphenyl)quinolin-2[1H]-one (–)-(1S,3'R,4a'R,6'S,8a'S)-3',4',4a',5',6',7',8',8a')-Octahydro-6'-((4'-methoxyphenyl)-methyl)quinolin-2'[1'H]-on-3'-yl)methyl(1-(1-naphthalenyl))carbamate (0.39 g prepared according to Example 18) was suspended in benzene (6.6 ml) containing triethylamine (0.12 ml). Trichlorosilane (0.089 ml) in benzene (1.5 ml) was added and the mixture was left to stir 1½ hours. The reaction was quenched by adding to saturated ammonium chloride solution. The organic layer was separated and the aqeuous layer was extracted into ethyl acetate. The organic layers were combined, dried (MgSO$_4$) and evaporated under reduced pressure. The residue was washed through a silica bed using ethyl acetate and then methanol as eluent. The solvent was evaporated under reduced pressure and the residue was purified by chromatography on a Dynamax 60A 21.6×250 mm column with 1.8% methanol and 0.25% ammonium hydroxide as eluent. The flow rate used was 21.6 ml/min and the product eluted at 22 minutes. The solvent was evaporated under reduced pressure to give the title compound (0.14 g,) mp 176°–178° C., $[\alpha]_D^{26}$=–33°(1% CHCl$_3$).

Analysis: C$_{18}$H$_{25}$NO$_3$ requires: C, 71.3; H, 8.3; N, 4.6%
Found: C, 71.2; H, 8.4; N, 4.8%.

EXAMPLE 25

(1'S,4aR,8aS)-3,4,4a5,6,7,8a-Octahydro-6-((4'-Methoxyphen)methylidene)-1-(1'-phenylethyl)quinolin-2[1H]one A. Methyl Spiro(1,3-dioxolane-2,3')cyclohexa-6-[1H]one propionate. 1,4-Cyclohexanedione monoethylene ketal (100 g), pyrrolidine (80 ml) and p-toluene sulphonic acid (0.5 g) in toluene (500 ml) were refluxed for 18 hours and the water collected by means of a Dean and Stark apparatus. The toluene was removed under reduced pressure and the residue dissolved in methanol (500 ml), then treated dropwise with methyl acrylate (50 ml). The mixture was stirred at room temperature for 15 hours and a solution of 10% acetic acid was added to bring the mixture to a pH of about 5. Stirring was continued for a further 3 hours and the solvent was removed under reduced pressure. The residue was extracted with chloroform. The combined chloroform extracts were washed with sodium bicarbonate solution, water then dried (MgSO$_4$) and evaporated to give an oil. This was distilled at 128°–132° C. under a pressure of 0.05 mm of Hg to give (89.4 g) of the required title product of step (A).

B. Methyl (1"S,1'R,2'S)spiro(1,3-dioxalone-2,3')-6-1"-phenylethylamino)-cyclohexanepropionate.

The product of step A, (21.26 g 0.087 m) and (S)-(–)-α-methylbenzylamine (10.51 g 0.087 m) in toluene (250 ml) were refluxed for 18 hours and water was collected by means of a Dean and Stark apparatus. The solvent was evaporated and the residue dissolved in ethanol (100 ml) and Raney nickel (ca. 10 g) was added. The mixture was hydrogenated at 50 psi for 3 days. The catalyst was removed by filtration and the solvent removed under reduced pressure. The resulting residue was purified by chromatography on silica using methyl acetate as eluent to give methyl (1"S,1'R,2'S)spiro (1,3-dioxalone-2,3')-6-(1"-phenylethylamino)cyclohexanepropionate (23.76 g).

C. (1"S,4a'R,8a'S)-3',4',4a',5',6',7',8',8a'-Octahydrospiro(1,3-dioxolane-2,6')-1'-(1"-phenylethyl)quinolin-2'[1H]-one The product of step B (22.7 g, 0.65 m) was refluxed for 4 hours in toluene (50 ml) and glacial acetic acid (3.92 g 0.065 m). The solution was cooled, then washed consecutively with sodium bicarbonate solution, 1N hydrochloric acid and water, then dried (MgSO$_4$) and evaporated to give (1"S,4'aR,8'aS)-3',4',4a',5',6',7',8',8a'-Octahydrospiro(1,3-dioxolane-2,6')-1'-(1"-phenylethyl)quinolin-2'[1H]-one, (18.78 g).

D. (1'S,4aR,8aS)-3,4,4a,5,6,7,8,8a-Octahydro-1-(1'phenylethyl)quinolin-2,6-dione.

The product of step C (18.7 g, 0.059m) with pyridinium p-toluene sulphonate (1.75 g) in acetone (90 ml) and water (10 ml) was refluxed for 60 hours. The solvent was removed under reduced pressure and the residue dissolved in ethyl acetate. The organic phase was washed with water, sodium bicarbonate solution, dried (MgSO$_4$) and evaporated. The residue was dissolved in acetone (180 ml) and water (20 ml) with pyridinium p-toluene sulphonate (1.75 g) and refluxed for 24 hours and the purification stage above repeated to give (1'S,4aR,8aS)-3,4,4a,5,6,7,8,8a-Octahydro-1-(1'-phenylethyl)-quinolin-2,6-dione (14.62 g) as a gum.

E. (1'S,4aR,8aS)-3,4,4a,5,6,7,8,8a-Octahydro-6-((4'-methoxyphenyl)methylidine)-1-(1'-phenylethyl)quinolin-2[1H]-one.

4-Methoxybenzyl triphenylphosphonium chloride (10.4 g, 0.25 m) in THF (250 ml) was cooled to –15° C. and treated with n-butyl lithium (1.6M solution in n-hexane, 15.5 ml) and allowed to warm to room temperature and stirred for 18 hours. The anion was cooled to –30° C. and the product of step D. (6.72 g 0.025 m) in THF (30 ml) was added and the mixture allowed to warm to room temperature. Water was added followed by ethyl acetate. The organic phase was separated, dried (MgSO$_4$) and evaporated. The mixture was triturated with diisopropyl ether and the solid removed by filtration and discarded. The resulting solution was evaporated to give a gum which was purified by chromatography on silica using ethyl acetate as eluent to give the title benzylidene as a 1:1 mixture of E- and Z-isomers (5.25 g).

EXAMPLE 26

(+)-(1'S,4aR,6R,8aS)-3,4,4a,5,6,7,8,8a-Octahydro-6-((4-methoxyphenyl)methyl)-1-(1'-phenylethyl)quinolin-2[1H]-one The benzylidene prepared according to Example 25 (8.3 g) with palladium black (1.0 g) in cyclohexane (100 ml) was refluxed for 24 hours and the catalyst removed by filtration. The solvent was removed under reduced pressure to give a gum. This was purified on silica using diethyl ester as eluent to give the title compound (5.0 g) as a gum. The gum was purified by repeating the chromatography, to give an analytical sample, $[\alpha]_D^{26}$=+16° (1% CHCl$_3$).

Analysis: C$_{25}$H$_{31}$NO$_2$.¼H$_2$O requires: C,78.6; H, 8.31; N, 3.67%
Found: C,78.9; H, 8.78; N, 3.63%.

EXAMPLE 27

(–)-(1'S,4aR,6S,8aS)-3,4,4a,5,6,7,8,8a-Octahydro-6-((4-methoxyphenyl)methyl)-1-(1'-phenylethyl)quinolin-2[1H]-one Further elution of the chromatographic purification step of Example 26 gave the title isomer as a white solid, mp 98–9° C., $[\alpha]_D^{27}$=–30° (1% CHCl$_3$).

Analysis: C$_{25}$H$_{31}$NO$_2$ requires: C, 79.5; H, 8.3; N, 3.7
Found: C, 79.3; H, 8.2; N, 3.6%.

EXAMPLE 28

(+)-(4aR,6R,8aS)-3,4,4a,5,6,7,8,8a-Octahydro-6-((4-methoxyphenyl)-methyl)quinolin-2[1H]-one (+)-(1'S,4aR,6R,8aS)-3,4,4a,5,6,7,8,8a-Octahydro-6-((4-methoxyphenyl)methyl)-1-(1'-phenylethyl)quinolin-2[1H] one (1.0 g prepared according to Example 26) in acetic acid (50 ml) with palladium hydroxide on carbon (Pearlman's catalyst, 0.1 g) was heated at 60° C. and hydrogenated at 50 psi for 24 hours. Further catalyst (0.1 g) was added and the mixture hydrogenated for a further 6 days. The catalyst was filtered and the solvent stirred under reduced pressure. The residue was dissolved in CHCl₃, then washed with sodium bicarbonate solution and dried (MgSO₄). The residue was triturated with diethyl ether and the solid collected by filtration. The solid was dissolved in CHCl₃ and passed through a short silica column eluted with chloroform. The solvent was evaporated to give the title compound (0.3 g) mp 197°–9° C.,$[\alpha]_D^{27}$=+80° (1% CHCl₃).

Analysis: $C_{17}H_{23}NO_2 \cdot \frac{1}{4} H_2O$ requires: C, 73.5; H, 8.5; N, 5.0

Found: C, 73.7; H, 8.6; N, 5.0%.

EXAMPLE 29

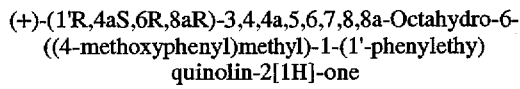
(+)-(1'R,4aS,6R,8aR)-3,4,4a,5,6,7,8,8a-Octahydro-6-((4-methoxyphenyl)methyl)-1-(1'-phenylethy)quinolin-2[1H]-one A. 4-Methoxybenzylcyclohexanone (43.68 g, 0.2 mol) was dissolved in toluene (250 ml). To this solution pyrrolidine (25 ml, 0.3 mol) was added together with a catalytic amount of toluene-4-sulphonic acid. The reaction mixture was refluxed with a Dean and Stark apparatus for 20 hours. Once the predicted amount of water had been collected, the solvent was removed under vacuum. Excess pyrrolidine was removed by adding a little toluene and evaporating under reduced pressure. The resulting liquid was dissolved in methanol (200 ml)and to the resulting stirred solution methyl acrylate (18 ml, 0.2 mol) dissolved in methanol (50 ml) was added dropwise. This was stirred for 20 hours at room temperature. The resulting liquid was neutralised with sodium bicarbonate and the product extracted into dichloromethane. The solution was then passed through a bed of Florisil. The solvent was evaporated leaving an oil which was purified by distillation. distilled at 155° C., 0.05 mmHg.

B. 2-(2-Methoxycarbonylethyl)-4-(4-methoxybenzyl)cyclohexanone (34 g, 112 mmol) was heated at reflux with R(+)-α-methylbenzylamine (14.8 g 122 mmol) and toluene (500 ml) in the presence of a catalytic amount of p-toluenesulphonic acid using a Dean and Stark water separator. After 24 hours the reaction mixture was concentrated in vacuo, dissolved in absolute ethanol and hydrogenated over Raney nickel under 50 psi hydrogen at room temperature. After 4 days the catalyst was filtered off and the filtrate concentrated in vacuo. The isomer mixture was separated by chromatography on a silica column using diisopropylether as eluent to give methyl (1'R,1S,2R,5R)-5-((4-methoxyphenyl)methyol-2-(1'-phenylethylamino)ethylamino)cyclohexanepropionate (Rf0.35).

C. The product of step (B) (10 g) was heated in toluene (200 ml) in the presence of acetic acid (2 ml) for 24 hours. After cooling the acetic acid was removed by washing with a saturated aqueous sodium bicarbonate solution. The organic phase was separated, dried (Na₂SO₄) and evaporated. The residue was chromatographed on a silica column using diisopropyl ether as eluent to give the title compound, mp 103–4° C.

EXAMPLE 30

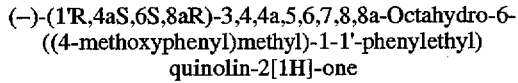
(−)-(1'R,4aS,6S,8aR)-3,4,4a,5,6,7,8,8a-Octahydro-6-((4-methoxyphenyl)methyl)-1-1'-phenylethyl)quinolin-2[1H]-one A. Also isolated from the chromatography step of Example 29 was methyl (1'R,1S,2R,5S)-5-((4-methoxyphenyl)methyl-2-(1'-phenylethylamino)cyclohexane-propionate having. an Rf value of 0.71.

B. The product of Step (A) (14 g 342 mmol) was heated under reflux in toluene (200 ml) in the presence of acetic acid (3 ml). After 24 hours further acetic acid was added (1 ml) and the mixture refluxed a further 4 hours. The reaction mixture was concentrated in vacuo and filtered through a pad of silica using diisopropylether as eluent. The filtrate was evaporated to give the title compound as an oil (12.2 g). This was crystallised from diisopropyl ether to crystals of the title compound, mp 68–9° C., $[\alpha]_D^{24}$=−27° (1% CHCl₃).

Analysis: $C_{25}H_{31}NO_2$ requires: C, 79.6; H, 8.3; N, 3.7%
Found: C, 79.7; H, 8.6; N, 3.8%.

EXAMPLE 31

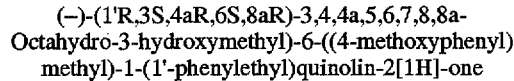
(−)-(1'R,3S,4aR,6S,8aR)-3,4,4a,5,6,7,8,8a-Octahydro-3-hydroxymethyl)-6-((4-methoxyphenyl)methyl)-1-(1'-phenylethyl)quinolin-2[1H]-one (−)-(1'R,4aS,6S,8aR)-3,4,4a,5,6,7,8,8a-Octahydro-6-((4-methoxyphenyl)methyl)-1-(1'-phenylethyl)quinolin-2[1H]-one (2 g, 5.3 mmol) in THF (5 ml) was added to lithium tetramethylpiperidide in THF (20 ml) under argon at −50° C. The reaction was allowed to warm to room temperature and was stirred for 2 hours. The resulting anion was treated with trimethylsilylethoxymethyl chloride (1 g, 6.0 mmol) at 0° C. then stirred at room temperature for 1 hour. Solvent was removed in vacuo and the residue partitioned between ethyl acetate and 2M HCl. The organic phase was separated, dried (Na₂SO₄) and concentrated to yield an oil. The oil was chromatographed on a silica column using diisopropyl ether as eluent and the major isomer was collected (0.8 g, 1.6 mmol). This was dissolved in dichloromethane (6 ml) and treated with BF₃.Et₂O (2 ml, 1.6 mmol) at room temperature and stirred for 10 minutes. The reaction mixture was diluted with dichloromethane (50 ml) washed with NaCO₃ solution, (15 ml), and the organic phase was separated, dried (Na₂SO₄) and concentrated to yield 0.7 g of an oil. Minor impurities were removed by chromatography on a silica column using ethyl acetate as eluent to give the title compound as an oil, $[\alpha]_D^{27}$=−7° (1% CHCl₃).

Analysis: $C_{26}H_{33}NO_2 \cdot \frac{1}{4} H_2O$ requires: C, 75.8; H, 8.2; N, 3.4

Found: C, 75.9; H, 8.5; N, 3.3%.

EXAMPLE 32

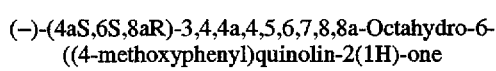
(−)-(4aS,6S,8aR)-3,4,4a,4,5,6,7,8,8a-Octahydro-6-((4-methoxyphenyl)quinolin-2(1H)-one (a) 2-(Methoxycarbonylethyl)-4-(4-methoxybenzyl)cyclohexanone (118 g, 0.399 mol) was dissolved in toluene (11) with R(+)-α-methylbenzylamine (52 g, 0.43 mol) and p-toluenesulphonic acid (0.2 g). The reaction mixture was heated under reflux in a Dean Stark apparatus for 24 hours. The solvent was removed under vacuum and the residue was hydrogenated in ethanol (800 ml) over Raney nickel at room temperature under 50 psi for four days. The catalyst was filtered off and the solvent of the filtrate was then evaporated under vacuum. The resulting oil was then chromatographed on silica with a diisopropyl ether and hexane solvent system (ratio 1:1). The first fraction yielded methyl (1'R,1S,2R,5S)-5-((4-methoxyphenyl)methyl)-2-(1'-phenylethylamino)-cyclohexanepropionate (50.5 g).

(b) The product of step (a) (18.78 g, 0.046 mol) was dissolved in the minimum amount of ether and diluted with hexane (200 ml), then treated with ethereal HCl. The solvent was evaporated and the solid was dissolved in methanol (200 ml) and added to a slurry of isopropanol and 10% palladium on carbon. The solution was then shaken in a Parr apparatus at 50° C. and at 50 psi under hydrogen for four days. The solution was filtered and the filtrate was then evaporated to give a cream solid. This was then treated with saturated sodium hydrogen carbonate and stirred for 2 hours. The solid was then filtered off and recrystallised from methanol to give the title compound, mp 199°–200° C. (7.38 g), $[\alpha]_D^{26}=-83°$ (1% CHCl$_3$).

Analysis C$_{17}$H$_{23}$NO$_2$ requires: C, 74.7; H, 8.5; H, 5.1% Found C, 74.3; H, 8.4; N, 5.1%.

EXAMPLE 33

(−)-(4aS,6S,8aR)Methyl-4-(1-(3,4,4a,5,6,7,8,8a-Octahydro-6-((4-methoxyphenyl)methyl)quinolin-2(1H)-one)methyl)benzoic acid A solution of methyl 4-(bromomethyl)benzoate (1.271 g, 0.005 mol) in toluene (10 ml) was added dropwise to the refluxing mixture of (−)-(4aS,6 S,8aR)-3,4,4a,5,6,7,8,8a-octahydro-6-((4-methoxyphenyl)methyl)quinolin-2(1H)-one (1.002 g, 0.0037 mol), powdered NaOH (0.42 g) and anhydrous potassium carbonate (0.74 g), tetraammonium hydrogen sulphate (0.1 g) and toluene (20 ml). The reaction mixture was refluxed for 4 days, cooled, diluted with toluene and then washed with water. The mixture was then dried over sodium sulphate, filtered and the solvent evaporated. The solid obtained was chromatographed on a silica gel column in ethyl acetate. The first fraction was collected and the solvent evaporated to give a solid which was recrystallised from acetonitrile to give the title compound (0.05 g) mp 151°–152° C., $[\alpha]_D^{27}32 -24°$ (1%, CHCl$_3$).

Analysis C$_{26}$H$_{31}$NO$_4$ requires: C, 74.1; H, 7.4; N, 3.3% Found C, 74.0; H, 7.5; N, 3.4%

EXAMPLE 34

(−)-(4aS,6S,8aR)-3,4,4a,5,6,7,8,8a-Octahydro-6-((4-methoxyphenyl)methyl)-1-(phenylmethyl)quinolin-2(1H)-one A solution of benzylbromide (0.44 ml, 0.0037 mol) in toluene (5 ml) was added dropwise to the refluxing mixture of (−)-(4aS,6S,8aR)-3,4,4a,5,6,7,8,8a-octahydro-6-((4-methoxyphenyl)methyl)quinolin-2(1H)-one (0.512 g, 0.0019 mol, prepared according to Example 32), powdered NaOH (0.175 g), potassium carbonate (0.35 g), tetraammonium hydrogen sulphate (0.02 g) and toluene (20 ml). The reaction was refluxed for 4 days. The reaction mixture was then cooled, diluted with toluene and then washed with water. It was then dried over sodium sulphate, filtered and the solvent evaporated. The solid was then chromatographed on a silica gel column in ethylacetate. The first fraction was collected, the solvent evaporated and the resulting solid recrystallised from acetonitrile to give the title compound (0.15 g), mp=118–9° C.; $[\alpha]_D^{25}=-10°$ (1%, CHCl$_3$).

Analysis C$_{24}$H$_{29}$NO$_2$ requires: C, 79.3; H, 8.0; N, 3.9 Found C, 79.0; H, 8.2; N, 3.9%

EXAMPLE 35

(+)-(1S',4aS,6R,8aS)-3,4,4a,5,6,7,8,8a-Octahydro-6-((4-Methoxyphenyl)-methyl)-1-(1'phenylethyl)quinolin-2(1H)-one Methyl (1'S,1S,2S,5R)-5-(4-methoxyphenyl)methyl)-2-(1'-phenylethylamino)-cyclohexanepropionate (1.59 g) (which is prepared by reductive amination of methyl 5-(4'-methoxyphenylmethyl)-2-oxo-cyclohexane propionate using S-(−)-α-methyl-benzylamine and sodium borohydride and isolating the desired amine by chromatography) and glacial acetic acid (0.31 g) in toluene (50 ml) were refluxed for 7 days. The solution was cooled, washed with sodium carbonate solution, dried (MgSO$_4$) and evaporated. The residue was purified by chromatography on silica using diethyl ether as eluent. The resulting solid was recrystallised from diisopropyl ether to give the title compound as a crystalline solid, (0.8 g); mp 121–2° C., $[\alpha]_D^{27}=+77°$ (1%, CHCl$_3$).

Analysis C$_{25}$H$_{31}$NO$_2$ requires: C, 79.5; H, 8.3; N, 3.7 Found C, 79.1; H, 8.4; N, 3.6%.

EXAMPLE 36

(+)-1'R,3S,4aR,6R,8aR)-3,4,4a,5,6,7,8,8a-Octahydro-3-hydroxymethyl-6-((4-methoxyphenyl)methyl)-1-(1'-phenylethyl(1)quinolin-2(1H)-one nBuLi (4.8 ml, 7.6 mmol) was added to (+)-bis [(R)-1-phenylethyl]amine, hydrochloride (1 g, 3.8 mmol) in THF (10 ml) at −20° C. and stirred for 15 minutes. (+)-(1'R,4aS,6R,8aR)-3,4,4a,5,6,7,8,8a-Octahydro-6-((4-methoxyphenyl)methyl)-1-(1'-phenylethyl)quinolin-2[1H]-one (1.44 g 3.8 mol) (prepared according to Example 29) in THF (3 ml) was added at −50° C., stirred for 15 minutes then allowed to warm to room temperature and stirred for 2 hours. The resulting anion was cooled to −50° C. and treated with trimethylsilylethoxymethyl chloride (0.64 g, 3.82 mmol), stirred for 15 minutes then allowed to warm to room temperature and stirred for 1 hour. The reaction mixture was quenched with 1M HCl, evaporated down and extracted into ethyl acetate. After drying (Na$_2$SO$_4$) and concentrating in vacuo, a colourless oil was obtained. The starting material was removed by column chromatography, on silica with ethylacetate as eluent. Fractions containing the protected title compound were collected and evaporated to give a solid. This product (2 g, 3.9 mol) dissolved in dichloromethane (20 ml) was treated with BF$_3$.Et$_2$O (6 ml, 19 mol) at room temperature and stirred for 10 minutes. The reaction mixture was partitioned between dichloromethane and saturated aqueous NaHCO$_3$ solution. An isomer mixture including the title compound was separated by column chromatography on silica-diisopropylether. The title compound was further purified by recrystallisation from di-isopropylether, mp 127–8° C., $[\alpha]_D^{23}=+82°$. (1%, CHCl$_3$)

Analysis C$_{26}$H$_{33}$NO$_3$ requires: C, 76.6; H, 8.1; N, 3.4 Found C, 76.5; H, 8.2; N, 3.4%

EXAMPLE 37

(−)-(1'R,3R,4aR,6S,8aR)-3,4,4a,5,6,7,8,8a-Octahydro-6-((4-methoxyphenyl)methyl)-3-methyl-1-(1'-phenylethyl)quinolin-2(1H)-one (−)-(1'R,4aS,6S,8aR)-3,4,4a,5,6,7,8,8a-Octahydro-6-((4-methoxyphenyl)methyl)-1-(1'-phenylethyl)quinolin-2[1H]-one (3 g, 8 mmol) prepared according to Example 30 in THF (7.5 ml) was added to LiTMP (nBuLi 5.4 ml, TMP 1.2 g, 8 mmol) in THF (30 ml) under argon at −70° C. The reaction was allowed to warm to room temperature and stirred for 2 hours. The resulting action was treated with CH$_3$I (1.36 g, 0.6 ml, 9.6 mmol) in THF (2 ml) at −70° C., allowed to warm to room temperature and stirred for 1 hour. The reaction mixture was evaporated down and the residue partitioned between ethyl acetate and 2M HCl. The organic phase was separated, dried (Na$_2$SO$_4$) and concentrated in vacuo. The resulting oil was chromatographed (silica-diisopropylether) and crystallised from hexane to give the title compound, (1.5 g), mp 108°–110° C., $[\alpha]_D^{26}=-13°$. (1%, CHCl$_3$).

Analysis C$_{26}$H$_{33}$NO$_2$ requires: C, 79.8; H, 8.6; N, 3.5%
Found: C, 79.4; H, 8.4; N, 3.6%.

EXAMPLE 38

(−)-(4aS,6S,8aR)-4-(1-(3,4a,5,6,7,8,8a-Octahydro-6-((4-methoxyphenyl)-methyl)quinolin-2-one)methyl) benzoic acid (−)-(4aS,6S,8aR)Methyl-4-(1-(3,4,4a,5,6,7,8,8a-octahydro-6-(4-methoxyphenyl)-methyl)quinolin-2(1H)-one)methylbenzoic acid (0.25 g mol) was dissolved in 1M NaOH in methanol (30 ml). The solution was heated and stirred for 4 hours and then neutralised with 1N HCl (aqueous). The title compound was then extracted into ethyl acetate (3 times) and the solvent evaporated to give the title compound (0.175 g), mp=110° C.–112° C., $[\alpha]_D^{25}=-40°$ (1%, CHCl$_3$).

Analysis C$_{25}$H$_{29}$NO$_4$. H$_2$O requires :C, 70.6; H, 7.3; N, 3.3
Found: C, 70.5; H, 7.5; N, 3.3%.

EXAMPLE 39

(−)-(1'R,4aR,6E,8aR)-1,3,4,4a,5,6,8,8a-Octahydro-6-((4methoxyphenyl)methylidene)-1-(1'-phenylethyl) quinolin-2-one A) 4-Methoxybenzyltriphenylphosphonium bromide (44 g, 95 mmol) in toluene (1.25 l) was refluxed for 18 hours and water collected by Dean-Stark apparatus. Half of the toluene was distilled off and the suspension allowed to cool at room temperature. THF (600 ml) was added and the mixture cooled to −15° C. then treated with nBuLi (59 ml, 95 mmol) under Ar. The solution was allowed to warm to 0° C. and was stirred for 2 hours.

B) 1,4-Cyclohexanedione monoethylene ketal (100 g 0.64 mol), pyrrolidine (80 ml, 0.96 mol) and p-toluenesulphonic acid (0.3 g) were heated under reflux in toluene (600 ml) with Dean-Stark water separation. After 3 hours the reaction was evaporated down under reduced pressure and the residue re-dissolved in toluene and concentrated again to give an oil. This oil was dissolved in methanol (500 ml) and treated with methyl acrylate (60 ml, 0.67 mol). The reaction was stirred at room temperature under Ar overnight. After 18 hours the reaction was evaporated in vacuo and the residual oil distilled at 132°–134° C. @0.2–0.1 mm Hg. The product (98 g, 0.4 mmol), R(+)-α-methylbenzylamine (50 g, 0.41 mol) and p-toluenesulphonic acid (0.3 g) were heated under reflux with Dean-Stark water separation in toluene (500 ml) for 24 hours. The toluene was evaporated off and the residual oil re-dissolved in methanol (250 ml), cooled to 0° C. and treated with sodium borohydride (15.2 g, 0.4 mol), portionwise. The reaction was stirred for 1 hour at room temperature, then quenched with water (250 ml). After stirring for 30 minutes the methanol was removed in vacuo and the residue partitioned between aqueous ammonia and diethyl ether. The organic phase was separated, dried (Na$_2$SO$_4$) and evaporated to give an oil. Glc on a SGE 25QC2 BT1, column showed the product to be a mixture of four isomers with the desired isomer having the longest retention time of 24.2 minutes. The desired isomer (−)-(1'R, 3R,4R)-spiro(1,3-dioxalane-2,5')-4'-(1"-phenylethylamino) cyclohex-3'-ane, propanoic acid, methyl ester was isolated by chromatography on SiO$_2$-diisopropylether yielding 38.5 of product.

C) The isomer from step B (36 g, 0.1 mol) was heated under reflux in toluene (1.5l) with glacial acetic acid (6 ml, 0.1 mol) for 5 hours. The solution was cooled, washed with saturated aqueous sodium bicarbonate solution, dried (Na$_2$SO$_4$) and concentrated in vacuo. The spiro ketal product was chromatographed on SiO$_2$-ethyl acetate and then heated under reflux in 20% aqueous acetic acid, (300 ml) for 4 hours. The reaction was diluted with water, extracted into diethyl ether, the organic phase washed with saturated sodium bicarbonate solution, dried (Na$_2$SO$_4$) and evaporated in vacuo. The resulting product was recrystallised from diisopropyl ether yielding 4aR, 8aR-3,4,4a,5,6,7,8,8a-octahydro-(R-1'phenylethyl)1H-2,6-dioxoquinoline, mp 126°–127° C.

D) The product of step C) previously dried by azeotroping with toluene, (25 g 92 mmol) in THF (200 ml) was added slowly to the anion produced in step A) keeping the temperature below 5° C. After stirring for 5 days the triphenylphosphine oxide formed was filtered off and washed with ethyl acetate. The filtrates were evaporated down yielding an oil, which crystallised from ethyl acetate. The mother liquors were filtered through a short pad of SiO$_2$ in ethyl acetate, and the filtrate chromatographed on SiO$_2$ in ethyl acetate-di-isopropyl ether (2:3), yielding two fractions. The faster running fraction was the Z isomer and the slower the E isomer. The E isomer crystallised from di-isopropyl ether and was collected, mp 92°–94°$[\alpha]_D^{26}=-181°$ (1% CHCl$_3$).

Analysis: C$_{25}$H$_{29}$NO$_2$ requires: C, 79.9; H, 7.7; N, 3.7.
Found: C, 79.6; H, 7.8; N, 3.7%

EXAMPLE 40

(−)-(1'R,4aR,6R,8aR)-3,4,4a,5,6,7,8,8a-Octahydro-6-((4-methoxyphenyl)methyl-1-(1'-phenylethyl)-quinoline-2[1H]-one (−)-(1'R,4aR,6R,8aR)-1,3,4,4a,5,6,7,8,8a-Octahydro-6-((4-methoxyphenyl)methylidene)-1-(1'-phenylethyl)quinolin-2-one (20 g 53 mmol) (prepared according to Example 39) was reduced by transfer hydrogenation over palladium black (1 g) in cyclohexene (200 ml) at reflux for 18 hours. The catalyst was filtered off and the filtrate concentrated in vacuo. The resulting oil was crystallised from diisopropyl ether and then recrystallised from the same solvent mp=130°–2° C., $[\alpha]_D^{26}=-61°$ (1% CHCl$_3$).

Analysis: C$_{25}$H$_{31}$NO$_2$ requires: C, 79.6; H, 8.2; N, 3.7
Found: C, 79.3; H, 8.3; N, 3.7%

EXAMPLE 41

(+)-(1'S,3R,4aS,6R,8aS)-3,4,4a,5,6,7,8,8a-Octahydro-3-hydroxymethyl)-6-((4-methoxyphenyl) methyl)-1-1'-phnylethyl)quinolin-2[1H]-one (+)-(1'S,4aR,6R,8aS)-3,4,4a,5,6,7,8,8a-Octahydro-6-((4-methoxyphenyl)methyl)-1-(1'-phenylethyl)quinolin-2[1H]-one (9.43 g) in THF (100 ml) was added to LiTMP (17.2 ml, nBuLi, 3.88 g TMP) in THF (50 ml) at −70° C. The solution was stirred at this temperature for 1.5 hours and the resulting anion treated with trimethylsilylethoxymethyl chloride (4.832 g). The reaction mixture was allowed to warm up to room temperature and the solvent evaporated. The residue was treated with 2M HCl and ethyl acetate. The organic phase was separated and purified by chromatography (SiO$_2$-di-isopropyl ether) and the product that eluted first was collected, evaporated to give an oil 7.4 g. The oil in dichloromethane (50 ml) was treated dropwise with boron trifluoride diethyl etherate (19 ml), then stirred at room temperature for 20 minutes. Sodium carbonate solution was added very carefully and the organic phase separated, dried (MgSO$_4$) and evaporated to give a gum. This was crystallised from hexane/DIPE (1:1) to give a white crystalline solid (2.5 g) mp 75°–7° C. $[\alpha]_D^{26}=+77°$ (1% CHCl$_3$).

Analysis: C$_{26}$H$_{35}$NO$_3$ requires C, 76.6; H, 8.2; N, 3.4%
Found: C, 76.8; 8.3; 3.4%

EXAMPLE 42

(−)-(1'R,4aR,6S,8aR)-3,4,4a,5,6,7,8,8a-Octahydro-6-((4-methoxyphenyl)-methyl-1-(1'-phenylethyl) quinolin-2[1H]-one (−)-(1'R,4aR,6S,8aR))-1,3,4,4a,5,6,8,8a-Octahydro-6-((4-methoxyphenyl)methylidene)-1-(1'-phenylethyl) quinolin-2[1H]-one (7.3 g 19.4 mmol) in cyclohexene (50 ml) was stirred under reflux with palladium black (1 g) for hour. The catalyst was filtered off and the solvent removed under reduced pressure. The resulting oil was filtered through a short pad of silica in ethyl acetate, yielding a mixture of isomers including the title compound as an oil, 8 g. This was stirred in diisopropyl ether (100 ml) at room temperature for 3 days. The supernatant was decanted leaving a semi-crystalline mass which was fractionally recrystallised from diisopropyl ether-cyclohexane (1:1) to give the title compound, mp 177–119, $[\alpha]_D^{26}=-77°$ (1% CHCl$_3$).

Analysis: C$_{25}$H$_{31}$NO$_2$ requires: C, 79.5; H, 8.2; N, 3.7
Found: C, 79.3 H, 8.4; N, 3.7%.

EXAMPLE 43

(−)-1'R,3R,4aS,6R,8aR)-3Hydroxymethyl-3,4,4a,5,6,7,8,8a-octahydro-6-(4-methoxyphenylmethyl)-1-(1'-phenylethyl)quinolin-2[1H]-one (−)-(1'R,4aR,6R,8aR)-3,4,4a,5,6,8,8a-Octahydro-6-((4-methoxyphenyl)methyl-1-(1'-phenylethyl)quinolin-2[1H]-one (1 g, 2.7 mmol), prepared according to Example 40, in THF (5 ml) was added to LiTMP (1.85 ml, nBuLi, 0.39 g TMP, 2.8 mmol) in THF (10 ml) under Ar at −78° C. for 1½ hours and the resulting anion treated with trimethylsilylethoxymethyl chloride (0.49 g, 2.94 mmol). The reaction was allowed to warm to room temperature and stirred for 1 hour. The solvent was evaporated off and the residue partitioned between 2M HCl and ethyl acetate. The organic phase was separated, dried (Na$_2$SO$_4$) and concentrated in vacuo, yielding an oil (1.36 g). The oil (1.15 g) in dichloromethane (10 ml) was treated at 0° C. under Ar, with BF$_3$.OEt$_2$ (3.5 ml) and stirred for 15 minutes. The reaction was quenched with water, the organic phase separated and the aqueous layer extracted again with CH$_2$Cl$_2$. The combined CH$_2$Cl$_2$ layers were washed with saturated NaHCO$_3$ solution, dried (Na$_2$SO$_4$) and concentrated in vacuo to give 0.95 g of an oil. This was chromatographed (SiO$_2$-hexane/ethyl acetate. (2:1)). The fractions containing the title compound were collected, evaporated and the residue crystallised from di-isopropyl ether, mp 136–7° C., $[\alpha]_D^{27}=-40°$ (1% CHCl$_3$).

Analysis: C$_{26}$H$_{33}$NO$_3$ requires: C, 76.6; H, 8.2; N, 3.4
Found: C, 76.2; H, 8.3; N, 3.3%.

EXAMPLE 44

(+)-(1'S,4aS,6S,8aS)-3,4,4a,5,6,7,8,8a-Octahydro-6-((4-methoxyphenyl)methyl-1-(1'-phenylethyl) quinolin-2[1H]-one (−)-(1'S,4aS,6E,8aS)-1,3,4,4,a,5,7,8,8a-Octahydro-6-((4methoxyphenyl)methylidene)-1-(1'-phenylethyl)quinolin-2-one 19.4 g) (prepared according to Example 39 but using S-(−)-α-methylbenzylamine instead of R-(+)-α-methylbenzylamine) was reduced by transfer hydrogenation over palladium black (1 g) in cyclohexene (200 ml) at reflux for 18 hours. The catalyst was filtered off and the filtrate concentrated in vacuo. The resulting oil was crystallised from diisopropyl ether and then recrystallised from the same solvent mp=13–2° C., $[\alpha]_D^{27}=60°$ (1% CHCl$_3$)

Analysis: C$_{25}$H$_{31}$NO$_2$ requires: C, 79.6; H, 8.2; N, 3.7
Found: C, 79.2; H, 8.3; N, 3.7%

We claim:

1. A compound of generic formula:

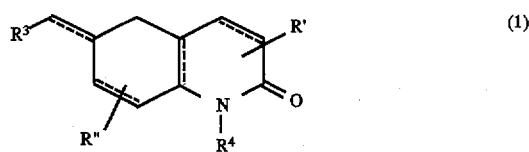 (1)

or a pharmaceutically acceptable salt thereof, where the dotted lines represent optional double bonds, R$^3$ is C$_6$–C$_{10}$ aryl optionally substituted by one or more substituents, the same or different, selected from halogen, halo-C$_1$–C$_6$ alkyl, halo-C$_1$–C$_6$ alkoxy, carboxy, hydroxy(C$_1$–C$_6$)alkyl, (C$_1$–C$_6$alkoxy) carbonyl, amino, mono- or di- (C$_1$–C$_6$ alkyl)amino, nitre, hydroxy, mercapto, C$_1$–C$_6$alkylthio, (C$_1$–C$_6$) alkyl carbonyl, (C$_6$–C$_{10}$ aryl)carbonyl, (C$_2$–C$_7$) alkanoyloxy, (C$_7$–C$_{11}$)aroyloxy, (C$_1$–C$_6$) alkylcarbonylamino, (C$_6$–C$_{10}$aryl)carbonylamino, (C$_2$–C$_7$) alkoxycarbonylamino, C$_6$–C$_{10}$aryl, C$_1$–C$_2$ alkylenedioxy; or C$_1$–C$_6$ alkyl or C$_1$–C$_6$ alkoxy or such groups substituted by C$_6$–C$_{10}$ aryl;

R$^4$ represents hydrogen, or a group of formula —CR$^a$R$^b$R$^c$ where R$^a$, R$^b$ and R$^c$ are independently selected from hydrogen, C$_1$–C$_6$ alkyl, and optionally substituted C$_6$–C$_{10}$ aryl;

R' represents one or more optional substituents, the same or different, selected from halogen, C$_1$–C$_6$ alkyl, C$_2$–C$_7$ alkoxycarbonyl, C$_1$–C$_6$ hydroxyalkyl, CN, aminocarbonyl, C$_2$–C$_7$ alkanoyloxy(C$_1$–C$_6$)alkyl, carboxy, C$_2$–C$_7$ alkoxylamino, halogen, halo C$_1$–C$_6$ alkyl, halo C$_1$–C$_6$ alkoxy, carboxy, hydroxy(C$_1$–C$_6$) alkyl, C$_2$–C$_7$ alkanoyloxy(C$_1$–C$_6$)alkyl, (C$_1$–C$_6$alkoxy) carbonyl, amino mono- or di-(C$_1$–C$_6$ alkyl)-amino, nitro, hydroxy, mercapto, C$_1$–C$_6$alkylthio, (C$_1$–C$_6$alkyl)carbonyl,(C$_6$–C$_{10}$ aryl)carbonyl, (C$_2$–C$_7$) alkanoyloxy, (C$_7$–C$_{11}$)aroyloxy, (C$_1$–C$_6$alkyl) carbonylamino, (C$_6$–C$_{10}$aryl)carbonylamino, (C$_2$–C$_7$ alkoxycarbonyl)amino, C$_6$–C$_{10}$ aryl, C$_1$–C$_2$ alkylenedioxy; (C$_6$–C$_{10}$ aryl optionally substituted by one or more substituents the same or different, selected from C$_1$–C$_6$ alkyl, C$_1$–C$_6$ alkoxy, or such groups substituted by C$_6$–C$_{10}$ aryl as defined above, and R" represents one or more optional mono- or di- valent substituents in the 5, 7 or 8 positions, the same or different, wherein the monovalent substituents are selected from C$_1$–C$_6$ alkyl, C$_2$–C$_7$ alkanoyloxy, hydroxy, amino, C$_2$–C$_7$ alkanoylamino, C$_1$–C$_6$alkylamino, or C$_1$–C$_6$ hydroxyalkyl, and R" can also represent hydroxy in the 6 position when the optional double bond is absent, and wherein the di-valent substituents are selected from oxo and methylene.

2. A compound having the formula

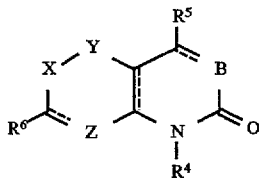

or a pharmaceutically acceptable salt thereof, wherein the dotted lines represent optional double bonds with the nitrogen ring optional bonds being between any adjacent ring atoms subject to valency considerations, B is a group of formula

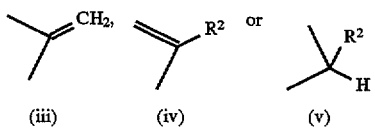

wherein $R^2$ is hydrogen, $C_1$–$C_6$ alkyl, $C_1$–$C_6$ hydroxyalkyl, $C_2$–$C_7$ alkanoyloxy($C_1$–$C_6$)alkyl, $C_2$–$C_7$ alkoxycarbonyl, cyano, aminocarbonyl, carboxy or $C_2$–$C_7$ alkanoylamino;

X is a group of formula

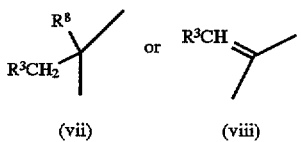

where $R^8$ is H or OH;

$R^3$ is a $C_6$–$C_{10}$ aryl optionally substituted by one or more substituents the same or different selective from halogen, $C_1$–$C_6$ alkyl; halogen, halo $C_1$–$C_6$ alkyl, halo $C_1$–$C_6$ alkoxy, carboxy, hydroxy($C_1$–$C_6$) alkyl, ($C_1$–$C_6$alkoxy)carbonyl, amino, mono- or di-($C_1$–$C_6$ alkyl)-amino, nitro, hydroxy, mercapto, $C_1$–$C_6$alkylthio, ($C_1$–$C_6$ alkyl) carbonyl, ($C_6$–$C_{10}$ aryl)carbonyl, ($C_2$–$C_7$)alkanoyloxy, ($C_7$–$C_{11}$) aroyloxy, ($C_1$–$C_6$ alkyl)carbonylamino, ($C_6$–$C_{10}$aryl)carbonylamino, ($C_2$–$C_7$) alkoxycarbonylamino, $C_1$–$C_2$ alkylenedioxy, $C_6$–$C_{10}$ aryl or ($C_6$–$C_{10}$ aryl)alkyl, said aryl being optionally substituted by one or more substituents, the same or different, selected from $C_1$–$C_6$ alkyl or $C_1$–$C_6$ alkoxy, or such groups substituted by $C_6$–$C_{10}$ aryl;

Y is

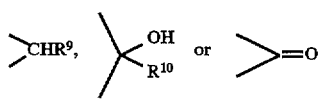

where $R^9$ represents hydrogen, $C_1$–$C_6$ alkyl, $C_2$–$C_7$ alkanoyloxy, or $CH_2OH$; and $R^{10}$ represents hydrogen or $C_1$–$C_6$ alkyl;

$R^4$ represents hydrogen, or a group of formula —$CR^aR^bR^c$ where $R^a$, $R^b$ and $R^c$ are independently selected from hydrogen, $C_1$–$C_6$ alkyl and $C_6$–$C_{10}$ aryl, where said aryl is optionally substituted as as defined under $R^3$;

Z is C=O, C=$CH_2$, —$CHR^7$—or=$C(R^7)$—where $R^7$ is hydrogen, OH, $CH_2OH$, $NH_2$, $C_2$–$C_7$ alkanoyloxy, $C_2$–$C_7$ alkanoylamino $C_1$–$C_6$alkylamino or a $C_1$–$C_6$ alkyl group optionally substituted by a group $R^3$ as defined above;

$R^5$ is hydrogen or $C_1$–$C_6$ alkyl; and $R^6$ is $NH_2$, $C_7$–$C_{17}$ aralkanoylamino, $C_2$–$C_7$ alkanoylamino or $R^6$ is one of the values listed for $R^5$ above.

3. A compound as claimed in claim 1 wherein $R^4$ is hydrogen or a group of formula —$CR^aR^bR^c$ where $R^a$ and $R^b$ are indepesndenfiy selected from hydrogen, methyl, ethyl, propyl, isopropyl or butyl and $R^c$ is selected from hydrogen, methyl, ethyl, isopropyl, propyl, butyl or a $C_6$–$C_{10}$ aryl.

4. A pharmaceutical composition comprising a compound of formula I

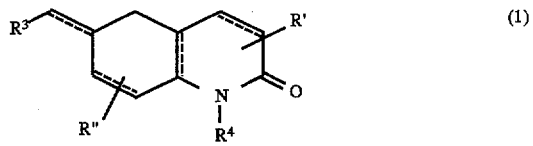

or a pharmaceutically acceptable salt thereof, where the dotted lines represent optional double bonds, $R^3$ is $C_6$–$C_{10}$ aryl optionally substituted by one or more substituents, the same or different, selected from $C_1$–$C_6$ alkyl or $C_1$–$C_6$ alkoxy or such groups substituted by $C_6$–$C_{10}$ aryl, halogen, halo-$C_1$–$C_6$ alkyl, halo-$C_1$–$C_6$ alkoxy, carboxy, hydroxy($C_1$–$C_6$)alkyl, ($C_1$–$C_6$alkoxy) carbonyl, amino, mono- or di- ($C_1$–$C_6$ alkyl)amino, nitro, hydroxy, mercapto, $C_1$–$C_6$alkylthio, ($C_1$–$C_6$) alkyl carbonyl, ($C_6$–$C_{10}$ aryl)carbonyl, ($C_2$–$C_7$) alkanoyloxy, ($C_7$–$C_{11}$)aroyloxy, ($C_1$–$C_6$) alkylcarbonylamino, ($C_6$–$C_{10}$aryl)carbonylamino, ($C_2$–$C_7$) alkoxycarbonylamino, $C_6$–$C_{10}$ aryl, or $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl;

R' represents one or more optional substituents, the same or different, selected from halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy($C_1$–$C_6$)alkyl, carboxy, $C_2$–$C_7$ alkoxyamino, $C_6$–$C_{10}$ aryl optionally substituted by one or more substituents, the same or different, selected from $C_1$–$C_6$ alkyl, $C_1$–$C_6$ alkoxy, or such groups substituted by $C_6C_{10}$ aryl as defined above; halogen, halo $C_1$–$C_6$ alkyl, halo $C_1$–$C_6$ alkoxy, carboxy, hydroxy($C_1$–$C_6$)alkyl, $C_2$–$C_7$ alkanoyloxy ($C_1$–$C_6$)alkyl, ($C_1$–$C_6$alkoxy)carbonyl, amino mono- or di-($C_1$–$C_6$ alkyl)-amino, nitro, hydroxy, mercapto, $C_1$–$C_6$alkylthio, ($C_1$–$C_6$alkyl)carbonyl,($C_6$–$C_{10}$ aryl) carbonyl, ($C_2$–$C_7$)alkanoyloxy, ($C_7$–$C_{11}$)aroyloxy, ($C_1$–$C_6$alkyl)carbonylamino, ($C_6$–$C_{10}$aryl) carbonylamino, ($C_2$–$C_7$ alkoxycarbonyl)amino, $C_6$–$C_{10}$ aryl, or $C_1$–$C_2$ alkylenedioxy; and R" represents one or more optional mono- or di- valent substituents in the 5, 7 or 8 positions the same or different wherein the monovalent substituents are selected from $C_1$–$C_6$ alkyl, $C_2$–$C_7$ alkanoyloxy, hydroxy, amino, $C_2$–$C_7$ alkanoylamino, $C_1$–$C_6$alkylamino, or $C_1$–$C_6$ hydroxyalkyl, and R" can also represent hydroxy in the 6 position when the optional double bond is absent, and wherein the di-valent substituents are selected from oxo and methylene.

5. A method of treating disorders in a mammal which are amenable to treatment by potassium ion channel blocking agents which comprises administration to the mammal needing treatment a therapeutically effective amount of a compound of the formula

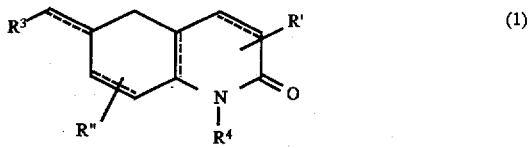
(1)

or a pharmaceutically acceptable salt thereof, where the dotted lines represent optional double bonds, $R^3$ is $C_6$–$C_{10}$ aryl optionally substituted by one or more substituents, the same or different, selected from $C_1$–$C_6$ alkyl or $C_1$–$C_6$ alkoxy or such groups substituted by $C_6$–$C_{10}$ aryl, halogen, halo-$C_1$–$C_6$ alkyl, halo-$C_1$–$C_6$ alkoxy, carboxy, hydroxy($C_1$–$C_6$)alkyl, ($C_1$–$C_6$alkoxy)carbonyl, amino, mono- or di- ($C_1$–$C_6$ alkyl)amino, nitro, hydroxy, mercapto, $C_1$–$C_6$alkylthio, ($C_1$–$C_6$alkyl carbonyl, ($C_6$–$C_{10}$ aryl)carbonyl, ($C_2$–$C_7$)alkanoyloxy, ($C_7$–$C_{11}$)aroyloxy, ($C_1$–$C_6$)alkylcarbonylamino, ($C_6$–$C_{10}$aryl)carbonylamino, ($C_2$–$C_7$) alkoxycarbonylamino, $C_6$–$C_{10}$ aryl, or $C_1$–$C_2$ alkylenedioxy;

R' represents hydrogen, or a group of formula —$CR^aR^bR^c$ where $R^a$, $R^b$ and $R^c$ are independently selected from hydrogen, $C_1$–$C_6$ alkyl, and optionally substituted $C_6$–$C_{10}$ aryl;

R' represents one or more optional substituents, the same or different, selected from halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy($C_1$–$C_6$)alkyl, carboxy, $C_2$–$C_7$ alkoxyamino, $C_6$–$C_{10}$ optionally substituted by one or more substituents the same or different, selected from $C_1$–$C_6$ alkyl, $C_1$–$C_6$ alkoxy, or such groups substituted by $C_6$–$C_{10}$ aryl as defined above; halogen, halo $C_1$–$C_6$ alkyl, halo $C_1$–$C_6$ alkoxy, carboxy, hydroxy,($C_1$–$C_6$)alkyl, $C_2$–$C_7$ alkanoyloxy ($C_1$–$C_6$)alkyl, ($C_1$–$C_6$ alkoxy)carbonyl, amino mono- or di-($C_1$–$C_6$ alkyl)-amino, nitro, hydroxy, mercapto, $C_1$–$C_6$alkylthio, ($C_1$–$C_6$ alkyl)carbonyl,($C_6$–$C_{10}$ aryl) carbonyl, ($C_2$–$C_7$)alkanoyloxy, ($C_7$–$C_{11}$)aroyloxy, ($C_1$–$C_6$alkyl)carbonylamino, ($C_6$–$C_{10}$aryl) carbonylamino, ($_2$–$C_7$ alkoxycarbonyl)amino, $C_6$–$C_{10}$ aryl, or $C_1$–$C_2$ alkylenedioxy; and R" represents one or more optional mono- or di- valent substituents in the 5, 7 or 8 positions the same or different wherein the monovalent substituents are selected from $C_1$–$C_6$alkyl, $C_2$–$C_7$ alkanoyloxy, hydroxy, amino, $C_2$–$C_7$ alkanoylamino, $C_1$–$C_6$alkylamino, or $C_1$–$C_6$ hydroxyalkyl, and R" can also represent hydroxy in the 6 position when the optional double bond is absent, and wherein the di-valent substituents are selected from oxo and methylene.

6. A compound as claimed in claim 2 wherein X has formula (vii) wherein $R^8$ is hydrogen.

7. A compound as claimed in claim 2 where Y is $CH_2$.

8. A compound as claimed in claim 2 wherein Z is $CH_2$.

9. A compound as claimed in claim 2 wherein $R^5$ and $R^6$ are hydrogen.

10. A compound as claimed in claim 2 wherein $R^2$ is hydrogen, $C_1$–$C_6$ alkyl, $C_2$–$C_7$ alkoxycarbonyl, $C_2$–$C_7$ alkanoylamino, CN, $C_2$–$C_7$ alkanoyloxy($C_1$–$C_6$)alkyl or $CH_2OH$.

11. A compound as claimed in claim 1 in which the optional bonds are all absent.

12. A compound as claimed in claim 1 having the formula

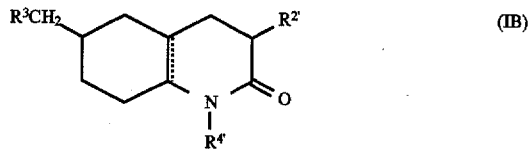
(IB)

in which formula $R^{2'}$ is hydrogen, $C_1$–$C_6$ alkyl, $C_2$–$C_7$ alkoxycarbonyl, acetylamino, CN or $CH_2OH$; $R^3$ is unsubstituted or substituted phenyl where the substituents is/are selected from $C_1$–$C_6$ alkyl, $C_1$–$C_6$ alkoxy, hydroxy, halogen and methylene- or ethylene-dioxy; and $R^{4'}$ is hydrogen, alkyl or optionally substituted aryl($C_1$–$C_6$) alkyl in which the alkyl group is itself optionally substituted by $C_1$–$C_6$ alkyl.

13. A compound of claim 1 which is 3,4,5,6,7,8-hexahydro-6-((4-hydroxyphenyl)methyl)-3-methylquinolin-2[1H]-one or a pharmaceutically acceptable salt thereof.

14. A compound of claim 1 which is ethyl 3,4,5,6,7,8-hexahydro-6-((4-methoxyphenyl)methyl)-quinolin-2[1H]-one-3-carboxylate or a pharmaceutically acceptable salt thereof.

15. A compound of claim 1 which is 3,4,5,6,7,8-hexahydro-6-((4-methoxyphenyl)methyl)quinolin-2[1H]-one or a pharmaceutically acceptable salt thereof.

16. A compound of claim 1 which is 3,4,5,6,7,8-hexahydro-6-((4-methoxyphenyl)methyl)quinolin-2[1H]-one-3-carbonitrile or a pharmaceutically acceptable salt thereof.

17. A compound of claim 1 which is 3,4,5,6,7,8-hexahydro-3-hydroxymethyl-6-((4-methoxyphenyl)methyl) quinolin-2[1H]-one or a pharmaceutically acceptable salt thereof.

18. A compound of claim 1 which is ethyl 3,4,4a,5,6,7,8,8a-octahydro-6-((4-methoxyphenyl)methyl)quinolin-2[1H]-one-3-carboxylate or a pharmaceutically acceptable salt thereof.

19. A compound of claim 1 which is 3,4,4a,5,6,7,8,8a-octahydro-3-hydroxymethyl-6-((4-methoxyphenyl)methyl) quinolin-2[1H]-one or a pharmaceutically acceptable salt thereof.

20. A compound of claim 1 which is 3,4,4a,5,6,7,8,8a-octahydro-3-hydroxymethyl-6-((4-hydroxyphenyl)-methyl)- quinolin-2[1H]-one or a pharmaceutically acceptable salt thereof.

21. A compound as claimed in claim 1 which is one of the following:

(±)-(3RS,4aRS,6SR,8aSR)3,4,4a,5,6,7,8,8a-octahydro-3-hydroxymethyl-6-((4-methoxyphenyl)methyl) quinolin-2[1H]-one;

(±)-(3RS,4aSR,6RS,8aRS)-3,4,4,4a,5,6,7,8,8a-octahydro-3-hydroxymethyl-6-((4-methoxyphenyl) methyl)quinolin-2[1H]-one;

(±)-(3SR,4aRS,6SR,8aRS)-3,4,4a,5,6,7,8,8a-octahydro-3-hydroxymethyl-6-((4-methoxyphenyl)methyl) quinolin-2[1H]-one;

(±)-(4aRS,6RS,8aSR)-3,4,4a,5,6,7,8,8a-octahydro-6-((4-methoxyphenyl)methyl)-quinolin-2[1H]-one;

(±)-(4aRS,6RS,8aRS)-3,4,4a,5,6,7,8,8a-octahydro-6-((4-methoxyphenyl)methyl)-quinolin-2[1H]-one;

(±)-(3S,4aS,6R,8aR)-3,4,4a,5,6,7,8a-octahydro-3-hydroxymethyl-6-(4-methoxy-phenyl)methylquinolin-2[1H]-one;

(±)-(3SR,4aRS,6SR,8aRS)-3,4,4a,5,6,7,8,8a-octahydro-3-hydroxymethyl-6-((4-methoxyphenyl)methyl)quinolin-2[1H]-one;

(±)-(3R,4aS,6R,8aS) or (3S,4aR,6S,8aR)-3,4,4a,5,6,7,8,8a-octahydro-3-hydroxymethyl-6-((4-methoxyphenyl)methyl)quinolin-2[1H]-one;

(')-(3R,4aS,6R,8aS) or (3S,4aR,6S,8aR)-3,4,4a,5,6,7,8,8a-octahydro-3-hydroxymethyl-6-((4-methoxyphenyl)methyl)quinol-2[1H]-one;

(−)-(3R,4aR,6S,8aS)-3,4,4a,5,6,7,8,8a-octahydro-3-hydroxymethyl-6-((4-methoxyphenyl)methyl)quinolin-2[1H]-one;

(1'S,4aR,8aS)-3,4,4a,5,6,7,8a-octahydro-6-((4'-methoxyphenyl)methylidene)-1-(1'-phenylethyl)quinolin-2[1H]-one;

(+)-(1'S,4aR,6R,8aS)-3,4,4a,5,6,7,8,8a-octahydro-6-((4-methoxyphenyl)methyl)-1-(1'-phenylethyl)quinolin-2[1H]-one;

(−)-(1'S,4aR,6S,8aS)-3,4,4a,5,6,7,8,8a-octahydro-6-((4-methoxyphenyl)methyl)-1-(1'-phenylethyl)quinolin-2[1H]-one;

(+)-(4aR,6R,8aS)-3,4,4a,5,6,7,8,8a-octahydro-6-((4-methoxyphenyl)-methyl)quinolin-2[1H]-one;

(+)-(1'R,4aS,6R,8aR)-3,4,4a,5,6,7,8,8a-octahydro-6-((4-methoxyphenyl)methyl)-1-(1'-phenylethyl)quinolin-2[1H]-one;

(−)-(1'R,4aS,6S,8aR)-3,4,4a,5,6,7,8,8a-octahydro-6-((4-methoxyphenyl)methyl)-1-(1'-phenylethyl)quinolin-2[1H]-one;

(−)-(1'R,3S,4aR,6S,8aR)-3,4,4a,5,6,7,8,8a-octahydro-3-hydroxymethyl-6-((4-methoxyphenyl)methyl)-1-(1'-phenylethyl)quinolin-2[1H]-one; or or a pharmaceutically acceptable salt thereof.

* * * * *